(12) United States Patent
Rehor et al.

(10) Patent No.: US 8,961,947 B2
(45) Date of Patent: Feb. 24, 2015

(54) POLYMERIC TISSUE SEALANT

(75) Inventors: Annemie Rehor, Winterthur (CH);
Simona Cerritelli, Zurich (CH)

(73) Assignee: Kuros Biosurgery AG (CH)

(*) Notice: Subject to any disclaimer, the term of this patent is extended or adjusted under 35 U.S.C. 154(b) by 1568 days.

(21) Appl. No.: 12/102,157

(22) Filed: Apr. 14, 2008

(65) Prior Publication Data

US 2008/0253987 A1  Oct. 16, 2008

Related U.S. Application Data

(60) Provisional application No. 60/911,737, filed on Apr. 13, 2007.

(51) Int. Cl.
| A61K 31/74 | (2006.01) |
| A61L 31/06 | (2006.01) |
| A61L 24/04 | (2006.01) |
| C08G 65/332 | (2006.01) |
| C08G 65/333 | (2006.01) |

(Continued)

(52) U.S. Cl.
CPC .............. *A61L 31/06* (2013.01); *A61L 24/046* (2013.01); *C08G 65/3322* (2013.01); *C08G 65/33306* (2013.01); *C08G 65/3342* (2013.01); *C08G 2650/58* (2013.01); *C08L 71/02* (2013.01)
USPC ...................................................... 424/78.17

(58) Field of Classification Search
None
See application file for complete search history.

(56) References Cited

U.S. PATENT DOCUMENTS 3,908,039 A  9/1975  Guthrie et al.
4,008,341 A  2/1977  Kehr (Continued)

FOREIGN PATENT DOCUMENTS

| CA | 2281602 | 8/1998 |
| EP | 1 348 045 | 3/1974 |

(Continued)

OTHER PUBLICATIONS

Cellesi, F., et al., "Towars a fully-synthetic substitute . . . ", 2004, Biomaterials, 25, pp. 5115-5124.*

(Continued)

*Primary Examiner* — Paul Dickinson
(74) *Attorney, Agent, or Firm* — Pabst Patent Group LLP

(57) ABSTRACT

Methods for making biomaterials for use as a tissue sealant, kits containing precursors for forming the biomaterials, and the resulting biomaterials are described herein. The biomaterials are formed from a composition comprising at least a first and a second precursor molecule, wherein:
i) the first precursor molecule is a poly(ethylene glycol) based polymer having x nucleophilic groups selected from the group consisting of thiol or amino groups, wherein x is greater than or equal to 2
ii) the second precursor molecule is of the general formula:

$$A\text{-}[(C_3H_6O)_n\text{---}(C_2H_4O)_m\text{---}B]_i$$

wherein m and n are integers from 1 to 200
i is greater than 2
A is a branch point
B is a conjugated unsaturated group The precursors are selected based on the desired properties of the biomaterial. Optionally, the biomaterials contain additives, such as thixotropic agents, radiopaque agents, or bioactive agents. In the preferred embodiment, the biomaterials are used to reduce, inhibit, or contain loss of a biological fluid or gas in a patient.

66 Claims, 4 Drawing Sheets

(51) Int. Cl.
*C08G 65/334* (2006.01)
*C08L 71/02* (2006.01)

(56) References Cited

U.S. PATENT DOCUMENTS

| | | |
|---|---|---|
| 4,086,196 A | 4/1978 | Tregear |
| 4,613,665 A | 9/1986 | Larm |
| 4,711,903 A | 12/1987 | Mueller et al. |
| 4,810,784 A | 3/1989 | Larm |
| 4,835,297 A | 5/1989 | Deschler et al. |
| 4,847,325 A | 7/1989 | Shadle et al. |
| 4,917,702 A | 4/1990 | Scheicher et al. |
| 5,100,668 A | 3/1992 | Edelman et al. |
| 5,162,430 A | 11/1992 | Rhee et al. |
| 5,171,670 A | 12/1992 | Kronenberg et al. |
| 5,202,247 A | 4/1993 | Kilburn et al. |
| 5,268,305 A | 12/1993 | Ribi et al. |
| 5,292,514 A | 3/1994 | Capecchi et al. |
| 5,294,690 A | 3/1994 | Iguchi et al. |
| 5,324,775 A | 6/1994 | Rhee et al. |
| 5,328,955 A | 7/1994 | Rhee et al. |
| 5,330,911 A | 7/1994 | Hubbell et al. |
| 5,413,791 A | 5/1995 | Rhee et al. |
| 5,426,148 A | 6/1995 | Tucker |
| 5,427,915 A | 6/1995 | Ribi et al. |
| 5,428,014 A | 6/1995 | Labroo et al. |
| 5,446,090 A | 8/1995 | Harris |
| 5,475,052 A | 12/1995 | Rhee et al. |
| 5,504,001 A | 4/1996 | Foster |
| 5,510,370 A | 4/1996 | Hock |
| 5,514,379 A | 5/1996 | Weissleder et al. |
| 5,527,856 A | 6/1996 | Rhee et al. |
| 5,529,914 A | 6/1996 | Hubbell et al. |
| 5,529,986 A | 6/1996 | Larsson et al. |
| 5,550,187 A | 8/1996 | Rhee et al. |
| 5,561,982 A | 10/1996 | Tunkel et al. |
| 5,567,422 A | 10/1996 | Greenwald |
| 5,573,934 A | 11/1996 | Hubbell et al. |
| 5,582,862 A | 12/1996 | Reed |
| 5,583,114 A | 12/1996 | Barrows et al. |
| 5,612,390 A | 3/1997 | Iguchi et al. |
| 5,626,863 A | 5/1997 | Hubbell et al. |
| 5,635,207 A | 6/1997 | Grinstaff et al. |
| 5,641,670 A | 6/1997 | Treco et al. |
| 5,693,341 A | 12/1997 | Schroeder et al. |
| 5,747,456 A | 5/1998 | Chorev et al. |
| 5,752,974 A | 5/1998 | Rhee et al. |
| 5,773,577 A | 6/1998 | Cappello |
| 5,814,603 A | 9/1998 | Oldenburg et al. |
| 5,840,837 A | 11/1998 | Krstenansky et al. |
| 5,874,308 A | 2/1999 | Kilburn et al. |
| 5,874,500 A | 2/1999 | Rhee et al. |
| 5,876,805 A | 3/1999 | Ostlie |
| 5,877,153 A | 3/1999 | Harris et al. |
| 5,897,955 A | 4/1999 | Drumheller |
| 5,932,462 A | 8/1999 | Harris et al. |
| 5,958,874 A | 9/1999 | Clark et al. |
| 6,051,648 A | 4/2000 | Rhee et al. |
| 6,054,122 A | 4/2000 | MacPhee et al. |
| 6,117,425 A | 9/2000 | MacPhee et al. |
| 6,136,564 A | 10/2000 | Kopetzki et al. |
| 6,165,486 A | 12/2000 | Marra |
| 6,166,130 A | 12/2000 | Rhee et al. |
| 6,197,325 B1 | 3/2001 | MacPhee et al. |
| 6,258,351 B1 | 7/2001 | Harris |
| 6,277,502 B1 | 8/2001 | Buchecker et al. |
| 6,312,725 B1 | 11/2001 | Wallace et al. |
| 6,331,422 B1 | 12/2001 | Hubbell |
| 6,384,107 B2 | 5/2002 | Liu |
| 6,458,889 B1 | 10/2002 | Trollsas et al. |
| 6,468,731 B1 | 10/2002 | Hubbell |
| 6,506,730 B1 | 1/2003 | Lee et al. |
| 6,534,591 B2 | 3/2003 | Rhee et al. |
| 6,559,119 B1 | 5/2003 | Burgess et al. |
| 6,566,406 B1 | 5/2003 | Pathak et al. |
| 6,624,245 B2 | 9/2003 | Wallace et al. |
| 6,653,420 B2 | 11/2003 | Domschke et al. |
| 6,818,018 B1 | 11/2004 | Sawhney |
| 6,833,408 B2 | 12/2004 | Sehl et al. |
| 6,887,974 B2 | 5/2005 | Pathak |
| 6,894,022 B1 | 5/2005 | Hubbell et al. |
| 6,958,212 B1 | 10/2005 | Hubbell et al. |
| 6,960,452 B2 | 11/2005 | Hubbell et al. |
| 7,009,034 B2 | 3/2006 | Pathak et al. |
| 7,026,292 B1 | 4/2006 | Lee et al. |
| 7,176,256 B2 | 2/2007 | Rhee et al. |
| 7,241,730 B2 | 7/2007 | Hubbell et al. |
| 7,247,609 B2 | 7/2007 | Lutolf et al. |
| 7,273,896 B2 | 9/2007 | Daniloff et al. |
| 7,291,673 B2 | 11/2007 | Hubbell |
| 7,332,566 B2 | 2/2008 | Pathak et al. |
| 7,413,739 B2 | 8/2008 | Hubbell |
| 7,575,740 B2 | 8/2009 | Molenberg |
| 7,670,605 B2 | 3/2010 | Hubbell |
| 7,744,912 B1 | 6/2010 | Hubbell |
| 2002/0091229 A1 | 7/2002 | Hubbell et al. |
| 2003/0044468 A1 | 3/2003 | Cellesi et al. |
| 2003/0059906 A1 | 3/2003 | Hubbell et al. |
| 2003/0103957 A1 | 6/2003 | McKerracher |
| 2003/0187232 A1 | 10/2003 | Hubbell et al. |
| 2003/0232944 A1 | 12/2003 | Molenberg et al. |
| 2004/0002770 A1 | 1/2004 | King |
| 2004/0202625 A1 | 10/2004 | Daniloff et al. |
| 2004/0235708 A1 | 11/2004 | Rhee et al. |
| 2005/0027069 A1 | 2/2005 | Rhee et al. |
| 2005/0027070 A1 | 2/2005 | Rhee et al. |
| 2005/0245721 A1 | 11/2005 | Beckley et al. |
| 2006/0147443 A1 | 7/2006 | Schense et al. |
| 2007/0010440 A1 | 1/2007 | Schense et al. |
| 2007/0032568 A1 | 2/2007 | Lin et al. |

FOREIGN PATENT DOCUMENTS

| | | |
|---|---|---|
| EP | 725 145 | 8/1996 |
| EP | 950 665 | 10/1999 |
| EP | 200 10 297 | 8/2000 |
| EP | 1 462 501 | 9/2004 |
| EP | 1 593 727 | 11/2005 |
| WO | WO 89/00051 | 1/1989 |
| WO | WO 90/05177 | 5/1990 |
| WO | WO 92/02238 | 2/1992 |
| WO | WO 92/02620 | 2/1992 |
| WO | WO 92/09301 | 6/1992 |
| WO | WO 92/22312 | 12/1992 |
| WO | WO 94/20133 | 9/1994 |
| WO | WO 95/05396 | 2/1995 |
| WO | WO 95/23611 | 9/1995 |
| WO | WO 96/03159 | 2/1996 |
| WO | WO 96/17633 | 6/1996 |
| WO | WO 97/18314 | 5/1997 |
| WO | WO 97/22371 | 6/1997 |
| WO | WO 99/31137 | 6/1999 |
| WO | WO 00/09087 | 2/2000 |
| WO | WO 00/10596 | 3/2000 |
| WO | WO 00/33764 | 6/2000 |
| WO | WO 00/44808 | 8/2000 |
| WO | WO 00/64481 | 11/2000 |
| WO | WO 00/64959 | 11/2000 |
| WO | 0116210 | 3/2001 |
| WO | WO 01/54746 | 8/2001 |
| WO | WO 02/085422 | 10/2002 |
| WO | WO 03/040235 | 5/2003 |
| WO | WO 03/052091 | 6/2003 |
| WO | WO 03/080144 | 10/2003 |
| WO | WO 2004/042068 | 5/2004 |
| WO | WO 2004/071543 | 8/2004 |
| WO | WO 2006/067221 | 6/2006 |
| WO | WO 2006/072623 | 7/2006 |

OTHER PUBLICATIONS

Adams, et al., "Roles of ephrinB ligands and EphB receptors in cardiovascular development: demarcation of arterial/venous domains, vascular morphogenesis, and sprouting angiogenesis,"

(56) References Cited

OTHER PUBLICATIONS

*Genes & Development* 13:295-306 (1999).
Approximate values of Youngs modulus (E) in MPa (date stamped Aug. 19, 1996).
Baumgartner, et al., "Constitutive expression of phVEGF165 after intramuscular gene transfer promotes collateral vessel development in patients with critical limb ischemia," *Circulation*, 97:1114-1123 (1998).
Besson, et al., "Synthetic peptide substrates for a conductimetric assay of *Pseudomonas aeruginosa* elastase", *Analytical Biochemistry*, 237(2):216-223 (1996).
Blaess, et al., "Structural analysis of the sixth immunoglobulin-like domain of mouse neural cell adhesion molecule L1 and its interactions with $\alpha v\beta 3$, $\alpha IIb\beta 3$, and $\alpha 5\beta 1$ integrins," *J Neurochem*, 71:2615-2625 (1998).
Bonadio, et al., "Localized, direct plasmid gene delivery in vivo: prolonged therapy results in reproducible tissue regeneration" *Nat Med.*, 5(7):753-9 (1999).
Borrajo, et al., "Derivatized Cyclodextrins as peptidometics: Influence on Neurite Growth," *Bioorganic and Medicinal Chemistry Letters*, 7:1185-90 (1997).
Braatz, et al. "A new hydrophilic polymer for biomaterial coatings with low protein adsorption", *J. Biomater. Sci. Polym. Ed.*, 3(6):451-62 (1992).
Brooks, et al., "Requirement of vascular integrin $\alpha v\beta 3$ for angiogenesis," *Science*, 264:569-571 (1994).
Brueckner, "EphrinB ligands recruit GRIP family PDZ adaptor proteins into raft membrane microdomains," *Neuron*, 22:511-524 (1999).
Calderwood, et al., "Integrins and actin filaments: reciprocal regulation of cell adhesion and signaling," *J Biol Chem*, 275:22607-22610 (2000).
Camarata, et al., "Sustained Release of Nerve Growth Factor from Biodegradable Polymer Microspheres," *Neurosurgery Online*, 30(3) 313-319 (1992).
Campbell, et al., "Evaluation of absorbable surgical sealants: In vitro testing", *Confluent Surgical, Inc.*, pp. 1-4 (2005).
Cardin, et al., "Molecular Modeling of Protein-Glycosaminoglycan Interactions," *Arterioscler Thromb Vasc Biol*, 9:21-32 (1989).
Carr et al., "Effects of ionic and nonionic contrast media on clot structure, platelet function and thrombolysis mediated by tissue plasminogen activator in plasma clots", *Haemostasis*, 25(4):172-81 (1995).
Conover, et al., "Disruption of Eph/ephrin signaling affects migration and proliferation in the adult subventricular zone," *Nature Neuroscience*, 3(11):1091-3324 (2000).
Coombs, et al., "Directing sequence-specific proteolysis to new targets. The influence of loop size and target sequence on selective proteolysis by tissue-type plasminogen activator and urokinase-type plasminogen activator", *J. Biol. Chem.*, 273(8):4323-4328 (1998).
Coussons, et al. "Factors that govern the specificity of transglutaminase-catalysed modification of proteins and peptides" *Biochemical L.*, 282:929-30 (1992).
Dalva, et al., "EphB receptors interact with NMDA receptors and regulate excitatory synapse formulation," *Cell*, 103:945-956 (2000).
Deblois, et al., "Heparin-fibroblast growth factor-fibrin complex: in vitro and in vivo applications to collagen-based materials", *Biomaterials.*, 15(9):665-72 (1994).
Dedhar & Hannigan, "Integrin cytoplasmic interactions and bidirectional transmembrane signaling," *Current Opinion in Cell Biology*, 8:657-669 (1996).
Deramond, et al., "Percutaneous vertebroplasty with polymethylmethacrylate. Technique, indications, and results." 36(3): 533-546 (1998).
Dimilla, et al., "Mathematical model for the effects of adhesion and mechanics on cell migration speed," *Biophys. J.*, 60(1):15-37 (1991).
Dinbergds, et al., "Cellular response to transforming growth factor-betal and basic fibroblast growth factor depends on release kinetics and extracellular matrix interactions," *J. Biol. Chem.*, 271(47):29822-9 (1996).

Downs, et al., "Calcium Alginate Beads as a Slow-Release System for Delivering Angiogenic Molecules in Vivo and in Vitro," *Journal of Cellular Physiology*, 152:422-429 (1992).
Edelman, et al., "Basic fibroblast growth factor enhances the coupling of intimal hyperplasia and proliferation of vasa vasorum in injured rat arteries," *J. Clin. Invest.*, 89(2):465-73 (1992).
Edelman, et al., "Controlled and modulated release of basic fibroblast growth factor," *Biomaterials.*, 12(7):619-26 (1991).
Edelman, et al., "Perivascular and intravenous administration of basic fibroblast growth factor: vascular and solid organ deposition," *Proc. Natl. Acad. Sci. U. S. A.*, 90(4):1513-7 (1993).
Edgar, et al., "The heparin-binding domain of laminin is responsible for its effects on neurite outgrowth and neuronal survival," *EMBO J.*, 3(7):1463-8 (1984).
Eliceiri & Cheresh, "The role of $\alpha v$ integrins during angiogenesis: insights into potential mechanisms of action and clinical development," *Journal of Clinical Investigation*, 103:1227-1230 (1999).
Esposito & Caputo, "Mammalian transglutaminases. Identification of substrates as a key to physiological function and physiopathological relevance", *FEBS J.*, 272(3):615-31 (2005).
Fasol, et al., "Experimental use of a modified fibrin glue to induce site-directed angiogenesis from the aorta to the heart," *Journal of Thoracic and Cardiovascular Surgery*, 107:1432-9 (1994).
Felding-Habermann, et al., "A single immunoglobulin-like domain of the human neural cell adhesion molecule L1 supports adhesion by multiple and platelet integrins," *J Cell Biol*, 139:1567-1581 (1997).
Feng, et al., "Roles for ephrins in positionally selective synaptogenesis between motor neurons and muscle fibers," *Neuron*, 25:295-306 (2000).
Ferguson, et al., "Evaluation of adjacent segment failure following verteroplasty," *Trans. 47th Ann. Meet. ORS*, abstract 0280 (2001).
Ferrara & Alitalo, "Clinical applications of angiogenic growth factors and their inhibitors," *Nature Medicine*, 5:1359-1364 (1999).
Ferrara, "Molecular and biological properties of vascular endothelial growth factor," *J Mol Med*, 77:527-543 (1999).
Folkman, "Angiogenesis in cancer, vascular , rheumatoid and other disease," *Nature Medicine*, 1:27-31 (1995).
Friedman, et al., "Relative Nucleophilic Reactivities of Amino Groups and Mercaptide Ions in Addition Reactions with $\alpha,\beta$-Unsaturated Compounds1,2", *J. Am. Chem. Soc.*, 87(16): 3672-3682 (1965).
Gale, et al., "Ephrin-B2 selectivity marks arterial vessels and neovascularization sites in the adult, with expression in both endothelial and smooth-muscle cells," *Developmental Biology*, 230:151-160 (2001).
Giannelli, et al., "Transforming growth factor-betal triggers hepatocellular carcinoma invasiveness via alpha3beta1 integrin", *Am J Pathol.*, 161(1):183-93 (2002).
Götz, et al., "Neurotrophin-6 is a new member of the nerve growth factor family," *Nature*, 372(6503):266-9 (1994).
Grainger, et al., "Poly(dimethylsiloxane)-poly(ethylene oxide)-heparin block copolymers. I. Synthesis and Characterization," *J. Biomed. Mater Res.*, 22(3): 231-249 (1988).
Greisler, et al., "Enhanced endothelial of expanded polyethrafluoroethylene grafts by fibroblast growth factor type 1 pretreatment," *Surgery*, 112:244-255 (1992).
Groenen, et al., "The carboxy-terminal lysine of alpha B-crystallin is an amine-donor substrate for tissue transglutaminase", *Eur J Biochem.*, 205(2):671-4 (1992).
Grootjans, et al., "Substrate requirements for transglutaminases. Influence of the amino acid residue preceding the amine donor lysine in a native protein", *J Biol Chem.*, 270(39):22855-8 (1995).
Hall, "Molecular properties of fibrin-based matrices for promotion of angiogenesis in vitro," *Microvascular Research*, 62:315-326 (2001).
Hall, et al., "Trimerization of cell adhesion molecule L1 mimics clustered L1 expression on the cell surface: Influence on L1-Ligand interactions and on promotion of neurite outgrowth," *J of Neurochemistry*, 75:336-346 (2000).
Hammoud, et al., "Management of coronary artery disease: Therapeutic options in patients with diabetes," *J Am. Col. Cardiology*, 36:355-65 (2000).

(56) References Cited

OTHER PUBLICATIONS

Harada, et al., "Basic fibroblast growth factor improves myocardial function in chronically ischemic porcine hearts," *J. Clin. Invest.*, 94(2):623-30 (1994).
Hata, et al., "Binding of lipoprotein lipase to heparin. Identification of five critical residues in two distinct segments of the amino-terminal domain," *J. Biol. Chem.*, 268(12):8447-57 (1993).
Haugen, et al, "Central and peripheral neurite outgrowth differs in preference for heparin-binding versus integrin-binding sequences," *J. Neurosci.*, 12(6):2034-42 (1992).
Herbert, et al., "Effects of fibinolysis on neurite growth from dorsal root ganglia cultured in two- and three-dimensional fibrin gels," *J. Comp. Neurol.*, 365(3):380-91 (1996).
Herbert, et al., "Effects of fibrin micromorphology on neurite growth fro m dorsal root ganglia cultured in three-dimensional fibrin gels," *J. Biomed. Mat. Res.*, 40(4):551-9 (1998).
Hern, et al., "Incorporation of adhesion peptides into nonadhesive hydrogels useful for Tissue Resurfacing" *J. Biomed. Mater. Res.*, 39:266-276 (1998).
Houle & Johnson, "Nerve growth factor (NGF)-treated nitrocellulose enhances and directs the regeneration of adult rat dorsal root axons through intraspinal neural tissue transplants," *Neuroscience Letters*, 103:17-23 (1989).
Hubbell, "Bioactive biomaterials", *Curr. Opinion Biotechnol.*, 10(2):123-129 (1999).
Hubbell, "Incorporation of engineered VEGF variants in fibrin cell ingrowth matrices", *FASEB Journal*, 17(4-5): Abstract No. 349.14—XP009068972 (2003).
Humphries, "Integrin activation: the link between ligand binding and signal transduction," *Curr Opin Cell Biol*, 8:632-640 (1996).
Ilan, et al., "Distinct signal transduction pathways are utilized during the tube formation and survival phases of in vitro angiogenesis," *J of Cell Science*, 111:3621-3631 (1998).
Ingber & Folkman, "How does extracellular matrix control capillary morphogenesis?" *Cell*, 58:803-805 (1989).
Jeong, et al., "The fibronectin-binding domain of transglutaminase", *J Biol Chem.*, 270(10):5654-8 91995).
Kallapur, et al, "The neural cell adhesion molecule (NCAM) heparin binding domain binds to cell surface heparan sulfate proteoglycans," *J Neuro. Res.*, 33(4):538-48 (1992).
Kaneda, et al., "Midkine, a heparin-binding growth/differentiation factor, exhibits nerve cell adhesion and guidance activity for neurite outgrowth in vitro," *J. Biochem.*, 119(6):1150-6 (1996).
Kang, et al., "Selective stimulation of endothelial cell proliferation with inhibition of smooth muscle cell proliferation by fibroblast growth factor-1 plus heparin delivered from glue suspensions," *Surgery*, 118:280-287 (1995).
Kiguchi, et al., "Altered expression of epidermal growth factor receptor ligands in tumor promoter-treated mouse epidermis and in primary mouse skin tumors induced by an initiation-promotion protocol," *Mol. Carcinog.*, 22(2):73-83 (1998).
Kinosaki, et al., "Identification of heparin-binding stretches of a naturally occurring deleted variant of hepatocyte growth factor (dHGF)," *Biochim. Biophys. Acta.*, 1384(1):93-102 (1998).
Kleinman, et al., "The laminins: a family of basement membrane glycoproteins important in cell differentiation and tumor metastases," *Vitam. Horm.*, 47:161-86 (1993).
Lee, et al., "Analysis of affinity and structural selectivity in the binding of proteins to glycosaminoglycans: Development of a sensitive electrophoretic approach," *Biochemistry*, 88:2768-2772 (1991).
Lin, et al., "Purification and Initial Characterization of Rat B49 Glial Cell Line-Derived Neurotrophic Factor," *Journal of Neurochemistry*, 63(2):758-768 (1994).
Lopez, et al., "Basic fibroblast growth factor in a porcine model of chronic myocardial ischemia: a comparison of angiographic, echocardiographic and coronary flow parameters," *J. Pharmacol. Exp. Ther.*, 282(1):385-90 (1997).
Lopez, et al., "Local perivascular administration of basic fibroblast growth factor: drug delivery and toxicological evaluation," *Drug Metab. Dispos.*, 24(8):922-4 (1996).
Lorsordo, et al., "Gene therapy for myocardial angiogenesis. Initial clinical results with direct myocardial injection of phVEGFI65 as sole therapy for myocardial ischemia," *Circulation*, 98:2800-2804 (1998).
Ludbrook, et al., "The integrin alphavbeta3 is a receptor for the latency-associated peptides of transforming growth factors beta1 and beta3", *Biochem J.*, 369(Pt 2):311-8 (2003).
Luginbuehl, et al., "Localized delivery of growth factors for bone repair" *European Journal of Pharmaceutics and Biopharmaceutics*, 58:197-208 (2004).
Lutolf, "Synthesis and physicochemical characterization of end-linked poly(ethylene glycol)-co-peptide hydrogels formed by Michael-type addition", *Biomacromolecules*, 4(3): 713-722 (2003).
Lutolf, "Systematic modulation of Michael-type reactivity of thiols through the use of charged amino acids", *Bioconjugate Chemistry*, 12(6):1051-1056 (2001).
Lyon, et al., "The Interaction of the Transforming Growth Factor-$\beta$s with Heparin/Heparan Sulfate is Isoform-specific," *The Journal of Biological Chemistry*, 272(29):18000-18006 (1997).
Martin & Timpl, "Laminin and other basement membrane components," *Annu. Rev. Cell.Dev. Biol.*, 3:57-85 (1987).
Massia, et al., "An RGD spacing of 440 nm is sufficient for integrin alpha V beta 3-mediated fibroblast spreading and 140 nm for focal contact and stress fiber formation," *J. Cell. Biol.*, 114(5):1089-100 (1991).
Mathis, et al., "Percutaneous vertebroplasty: a developing standard of care for vertebral compression fractures," *Am. J. Neuroradiol.* 22: 373-381 (2001).
Maysinger, et al., "Microencapsulated nerve growth factor: effects on the forebrain neurons following devascularizing cortical lesions," *Neuroscience Letters*, 140:71-74 (1992).
McCaffrey, et al., "Transforming growth factor-beta 1 is a heparin-binding protein: identification of putative heparin-binding regions and isolation of heparins with varying affinity for TGF-beta 1," *J. Cell. Physiol.*, 152(2):430-40 (1992).
Michel, et al., "Compressive fatigue behavior of bovine trabecular bone," *J. Biomechanics* 26: 453-463 (1993).
Monsonego, et al., "Factor XIIIa as a nerve-associated transglutaminase", *FASEB J.*, 12(12):1163-71 (1998).
Montgomery, et al., "Human neural cell adhesion molecule L1 and Rat homologue NILE are ligands for integrin $\alpha\gamma\beta 3$," *J Cell Biol*, 132:475-485 (1996).
Nakayama and Matsuda, "Photocurable surgical tissue adhesive glues composed of photoreactive gelatin and poly(ethylene glycol) diacrylate", *J. Biomed. Mater. Res.*, 1999;48(4):511-21.
Nehls and Herrmann, "The configuration of fibrin clots determine capillary morphogenesis and endothelial cell migration," *Microvascular Research*, 51:347-364 (1996).
Nesti, et al., "TGF-betal calcium signaling increases alpha5 integrin expression in osteoblasts", *J Orthop Res.*, 20(5):1042-9 (2002).
Netzel-Arnett, et al., "Sequence specificities of human fibroblast and neutrophil collagenases", *J. Biol. Chem.*, 266:6747-6755 (1991).
Nolo, et al., "Developmentally regulated neurite outgrowth response from dorsal root ganglion neurons to heparin-binding growth-associated molecule (HB-GAM) and the expression of HB-GAM in the targets of the developing dorsal root ganglion neurites," *Eur. J. Neurosci.*, 8(8):1658-65 (1996).
Pacioreck, et al. *Annual fall meeting of the BMES*, poster abstract P2. 199 (Sep. 26-29, 2007).
Pepper, et al., "Angiogenesis: a paradigm for balanced extracellular proteolysis cell migration and morphogenesis," *Enzyme Protein*, 49:138-162 (1996).
Potts, "Parathyroid hormone: past and present", *J Endocrinol.*, 187(3):311-25 (2005).
Powell, et al., "Controlled Release of nerve growth factor from a polymeric implant," *Brain Research* 515:309-311 (1990).
Presta, et al., "Structure-function relationship of basic fibroblast growth factor: site-directed mutagenesis of a putative heparin-binding and receptor-binding region," *Biochem. Biophys. Res. Commun.*, 185(3):1098-107 (1992).
Reddi, "Role of Morphogenetic Proteins in Skeletal Tissue Engineering and Regeneration," *Nature Biotechnol.*, 16:247-252 (1998).

(56) References Cited

OTHER PUBLICATIONS

Rixon, et al., "Do the non-catalytic polysaccharide-binding domains and linker regions enhance the biobleaching properties of modular xylanases?" *Appl. Microbiol. Biotechnol.*, 46(5-6): 514-520 (1996).
Rixon, et al., "Parathyroid hormone fragments may stimulate bone growth in ovariectomized rats by activating adenylyl cyclase", J Bone Miner. Res., 9(8):1179-89 (1994).
Rogers, et al., "Neuron-specific interactions with two neurite-promoting fragments of fibronectin," *J. Neurosci.*, 5(2):369-78 (1985).
Rosengart, et al., "Angiogenesis Gene Therapy. Phase I assessment of direct intramyocardial administration of an adenovirus expressing phVEGF165 cDNA to individuals with clinically significant severe coronary artery disease," *Circulation*, 100:468-474 (1999).
Rout, et al., "Transforming growth factor-beta1 modulates expression of adhesion and cytoskeletal proteins in human peritoneal fibroblasts", *Fertil Steril.*, 78(1):154-61 (2002).
Ruoslahti & Engvall, "Perspectives series: Cell adhesion in vascular biology," *J Clin Invest*, 99:1149-1152 (1997).
Sakata & Aoki, et al., "Cross-linking of α2-plasmin inhibitor to fibrin by fibrin-stabilizing factor," *J Clin Invest*, 65:290-297 (1980).
Sakiyama, et al., "Incorporation of heparin-binding peptides into fibrin gels enhances neurite extension: an example of designer matrices in tissue engineering," *FASEB J* 13(15): 2214-24 (1999).
Sakiyama-Elbert & Hubbell, "Controlled release of nerve growth factor from a heparin-containing fibrin-based cell ingrowth matrix" *Journal of Controlled Release*, 69:149-158 (2000).
Sakiyama-Elbert, et al., "Development of fibrin derivatives for controlled release of heparin binding growth factors," *J. Controlled Release*, 65(3) 389-402 (2000).
Sakiyama-Elbert, et al., "Development of growth factor fusion proteins for cell-triggered drug delivery" *FASEB J.*, 15:1300-1302 (2001).
Sanborn, "In situ crosslinking of a biomimetic peptide-PEG hydrogel via thermally triggered activation of factor XIII", *Biomaterials*, 23(13):2703-2710 (2002).
Saraph, et al., "Treatment of unicameral calcaneal bone cysts in children: review of literature and results using a cannulated screw for continuous decompression of the cyst", *J. Pediatr. Orthop.*, 24(5):568-73 (2004).
Sato, "Enzymatic procedure for site-specific pegylation of proteins", *Advanced Drug Delivery Reviews*, 54(4):487-504 (2002).
Sakata & Aoki, et al., "Cross-linking of 2-plasmin inhibitor to fibrin by fibrin-stabilizing factor," *J Clin Invest*, 65:290-297 (1980).
Sato Haruya, "Enzymatic procedure for site-specific pegylation of proteins", *Advanced Drug Delivery Reviews*, 54(4):487-504 (2002).
Spillman, et al., "Defining the interleukin-8-binding domain of heparan sulfate," *J. Biol. Chem.*, 273(25):15487-93 (1998).
Steffen, et al., "Characterization of cell-associated and soluble forms of connective tissue growth factor (CTGF) produced by fibroblast cells in vitro," *Growth Factors*, 15(3):199-213 (1998).
Stein, et al., "Eph receptors discriminate specific ligand oligomers to determine alternative signaling complexes, attachment, and assembly responses," *Genes & Development*, 12:667-678 (1998).
Studier, et al., "Use of T7 RNA polymerase to direct expression of cloned genes," *Methods Enzymol.* 185:60-89 (1990).
Takagi & Doolittle, "Amino acid sequence studies on the alpha chain of human fibrinogen. Location of four plasmin attack points and a covalent cross-linking site", *Biochem.*, 14:5149-5156 (1975).
Takeshita, et al., "Therapeutic Angiogenesis. A single intraarterial bolus of vascular endothelial growth factor augments revascularization in a rabbit ischemic hind limb model," *J Clin Invest*, 93:662-670 (1994).
Tashiro, et al., "A synthetic peptide containing the IKVAV sequence from the a chain of laminin mediates cell attachment, migration, and neurite outgrowth," *J. Biol. Chem.*, 264(27):16174-82 (1989).
Tessler, et al., "Heparin modulates the interaction of VEGF165 with soluble and cell associated flk-1 receptors," *J. Biol. Chem.*, 269(17):12456-61 (1994).
Thompson, et al., "Site-directed neovessel formation in vivo," *Science*, 241:1349-1352 (1988).
Tyler-Cross, et al., "Heparin binding domain peptides of antithrombin III: analysis by isothermal titration calorimetry and circular dichroism spectroscopy," *Protein Sci.*, 3(4):620-7 (1994).
Usui, et al., "Propolypeptide of von Willebrand factor serves as a substrate for factor XIIIa and is cross-linked to laminin", *J Biol Chem.*, 268(17):12311-6 (1993).
Wang, et al., "Molecular distinction and angiogenesis interaction between embryonic arteries and veins revealed by ephrin-B2 and its receptor Eph-B4," *Cell*, 93:741-753 (1998).
Weatherford, et al., "Vascular endothelial growth factor and heparin in a biologic glue promotes human aortic endothelial cell proliferation with aortic smooth muscle cell inhibition," *Surgery*, 433-439 (1996).
Yamada, "Adhesive recognition sequences," *J. Biol. Chem.*, 266(20):12809-12 (1991).
Yamada, et al., "Characterization of fibronectin interactions with glycosaminoglycans and identification of active proteolytic fragments", *J Biol Chem.*, 255(13):6055-63 (1980).
Yanish-Perron, et al., "Improved M13 phage cloning vectors and host strains: nucleotide sequences of the M13mp18 and pUC19 vectors," *Gene*, 33(1):103-19 (1985).
Zisch, "Cell-demanded release of VEGF from synthetic, biointeractive cell ingrowth matrices for vascularized tissue growth", *The FASEB Journal*, 17(15):1-25 (2003).
Zisch, et al., "Covalently conjugated VEGF-fibrin matrices for endothelialization", *Journal of Controlled Release*, 72:101-113 (2001).
Zucker & Katz, "Platelet factor 4: production, structure, and physiologic and immunologic action," *Proc. Soc. Exp. Biol. Med.*, 198(2):693-702 (1991).
Pacios, et al., "Structures and bonding in silane derivatives with one alkali atom" , J. Phys. Chem., 104:7617-7624 (2000).

* cited by examiner

POLYMERIC TISSUE SEALANT

CROSS-REFERENCE TO RELATED APPLICATION

This application claims priority to U.S. Ser. No. 60/911,737, filed Apr. 13, 2007, the disclosure of which is herein incorporated by reference.

FIELD OF THE INVENTION

The present invention relates to biomaterials and precursor molecules capable of forming biomaterials and methods of making and using thereof. In particular, the present invention relates to biomaterials for sealing or blocking tears, cuts, or abrasions in tissue.

BACKGROUND OF THE INVENTION

While performing medical procedures as part of a surgical intervention or treatment of injury, a physician must often deal with extravasation of body fluids, such as cerebrospinal fluids during brain or spinal surgery, or blood resulting from an injury, a disease or disorder, or from a surgical procedure. Restoring tissue and circulation integrity is important for a positive outcome of a treatment regardless of whether the damage was the result of an injury or a surgical procedure.

The oldest method of joining damaged tissues is the use of mechanical fasteners such as clamps, staples or sutures. Mechanical tissue fasteners suffer from a variety of limitations. Mechanical fasteners require significant skill, are time consuming to apply and can leak along the line of joinder, which can itself cause additional trauma to surrounding tissue. Also, mechanical fasteners can be ineffective in a number of highly vascularized organs. These disadvantages further slow the surgical procedure and healing time.

Attempts to overcome these disadvantages have resulted in the development of adhesives, glues or sealants capable of bonding tissue surfaces together rapidly, either alone, or in combination with mechanical fastening while promoting, or at least not inhibiting, normal healing and reducing or preventing the loss of body fluids.

A common class of tissue adhesives is fibrin-based materials, which contain a concentrate of fibrinogen and thrombin. The fibrin adhesives are typically two-component adhesives that when mixed together with a calcium source react to simulate the last stages of the naturally occurring blood clot-forming cascade. The resulting clot adheres to tissue and bridges tissue, gaps and seals tissue until healing can occur. However, fibrin-based adhesives have met with limited success owing to low strength of the sealing materials and the risk associated with using human blood derived products which may be contaminated.

Glues based on gelatin cross-linked with an aldehyde have also met with limited success. Representative of this class of glues are gelatin-resorcinol cross-linked with formaldehyde (GRF) or glutaraldehyde (GRFG). While gelatin-based glues have been extensively studied and shown to generally be effective, these compositions have met with limited success owing to the use of hot gelatin solutions, tissue irritation associated with the aldehyde, and the criticality of the handling procedures needed to obtain proper cross-linking at the joinder site.

Due to the above-described limitations, considerable development effort has been directed towards finding a suitable synthetic composition which can be used as tissue glues or sealants. To this end, cyanoacrylates, polyurethanes, poly-methylmethacrylates and polyethylene glycols, among other synthetic polymers, have been investigated as tissue glues or sealants with limited success. There are few available tissue glues or sealant compositions that meet the requirements of sufficient mechanical strength and biocompatibility, in addition to handling properties consistent with a wide variety of surgical settings.

However, these compositions show disadvantages with regard to handling and mechanical properties such as swelling of the biomaterial. Thus, there exists a need for a biomaterial that can be applied as a tissue glue or sealant that is not only biocompatible, but also has a well-defined cure and shows a combination of the required mechanical properties.

It is therefore an object of the present invention to provide compositions, methods and kits suitable for forming synthetic biomaterials for use as tissue sealant.

It is a further object of the invention to provide a synthetic biomaterial for use as tissue sealant which presents low increase in volume owing to water uptake.

It is a further object of the invention to provide a synthetic biomaterial for use as tissue sealant which is completely resorbable over time.

It is a further object of the invention to provide a synthetic biomaterial with good mechanical strength for use as tissue sealant.

It is a further object of the invention to provide a synthetic biomaterial that can potentially serve as an adjunct to sutured dural repair during cranial surgery and reduces or prevents leakage of cerebrospinal fluid into the external environment.

SUMMARY OF THE INVENTION

Compositions and methods for making biomaterials for use as tissue sealants, kits containing precursor molecules for forming the biomaterials, and the use of biomaterials are described herein. The compositions, which are used to make the biomaterials, comprise at least a first and a second precursor molecule. The first precursor molecule contains at least two nucleophilic groups, and the second precursor molecule contains at least two electrophilic groups. The nucleophilic and electrophilic groups of the first and second precursor molecules are capable of forming covalent linkages with each other under physiological conditions. The crosslinking preferably occurs in solution, such as aqueous solution, under basic conditions. The precursor molecules are selected based on the desired properties of the biomaterial. In one embodiment, the first precursor molecule is a poly(ethylene glycol) based polymer having x nucleophilic groups selected from the group consisting of thiol or amino groups, wherein x is greater than or equal to 2. Preferably, the x nucleophilic groups are thiol groups. Preferably the second precursor molecule is a multiarm poly(ethylene oxide-polypropylene oxide) (PEO-PPO) block copolymer functionalized on each of its arms with conjugated unsaturated groups and the second precursor molecule is of the general formula II:

$$A\text{-}[(C_3H_6O)_n\text{---}(C_2H_4O)_m\text{---}B]_i \qquad \text{Formula II}$$

wherein m and n are integers from 1 to 200;
i is greater than 2;
A is a branch point; and
B is a conjugated unsaturated group.

In a preferred embodiment, the first precursor molecule is a four-arm poly(ethylene glycol) (PEG) functionalized on each of its arms by a thiol group (pentaerythritol poly(ethylene glycol)ether tetra-sulfhydryl "PEG tetrathiol"). These polymers are commercially available from BASF under the tradename Tetronic®. In a most preferred embodiment, pentaerythritol poly(ethylene glycol)ether tetra-sulfhydryl has a molecular weight in a range of about 2 to 20 kD), more preferably in a range of about 3 to 11 kD and even more preferably in a range of about 5 to 10 kD. In another embodiment, the conjugated unsaturated groups B of the second precursor molecule are acrylate groups. Preferably, the branch point A of the second precursor molecule is selected from the group consisting of carbon, glycerol, pentaerythritol, dipentaerythritol and ethylene diamine. More preferably, the branch point A of the second precursor molecule is ethylene diamine. The second precursor molecule of formula II has a molecular weight in the range of about 10 to 25 kD, more preferably in the range of about 12 to 20 kD) and even more preferably in the range of about 14 to 18 kD. Preferably, each of the arms of the first or second precursor molecule has the same or similar polymerization degree. This means that each arm of the first or second precursor molecule has an identical or nearly identical molecular weight. Choosing precursor molecules wherein the sum of the number of nucleophilic groups and electrophilic groups is greater than or equal to five results in the formation of a three-dimensional network.

The compositions may contain one or more additives, such as colorants, thixotropic agents, radiopaque agents, fillers, stabilizers or bioactive agents. In a preferred embodiment, the composition contains a colorant selected from the group of methylene blue, lissamin green or fast green. The composition may also contain a base. In one embodiment, the base is sodium carbonate. In the preferred embodiment, the biomaterials formed from the compositions are used to reduce, inhibit, or contain loss of body fluids, such as loss of cerebrospinal fluid following brain and/or spinal surgery. In a preferred embodiment the compositions are used as medical sealant. In another preferred embodiment the compositions are used to coat the surface of a tissue. In another embodiment, the compositions are used for the manufacture of a medicament for effecting the non-surgical attachment of a first surface and a second surface.

In one embodiment, the biomaterials are made using a method comprising the steps of:
  i) providing a first precursor molecule;
  ii) providing a second precursor molecule; and
  iii) reacting the two precursor molecules in the presence of a basic solution to form a crosslinked three dimensional network.

Preferably the basic solution has a pH in a range of between 9 to 14, more preferably in a range of between 10 to 13, more preferably in a range of between 10 to 12. The pH of the solution resulting of steps i), ii) or iii) is preferably in a range of between 9 to 13, more preferably between 9.5 to 11.5, most preferably between 9.8 to 11 to allow for rapid gelation. Preferably, the basic solution is a sodium carbonate solution. After contacting the two precursor molecules with the basic solution, the biomaterial is rapidly formed, preferably the biomaterial is formed in less than two minutes, more preferably in less than 10 seconds and even more preferably in less than 5 seconds.

The precursor molecules can be stored separately as dry powders and/or in buffered solutions, typically having an acidic pH. In a preferred embodiment, the first precursor molecule is stored as a dry powder in a first container and the second precursor molecule is stored in an aqueous buffered solution having an acidic pH in a second container. Optionally, the base may be stored in solution in a third container. The precursor molecules can be in contact for minutes or hours prior to use. In one embodiment, the first precursor molecule and second precursor molecule are kept separated and are only mixed prior to transfer the resulting mixture in a dual compartment syringe. One compartment of the syringe comprises the mixture of the precursor molecules and the other compartment the basic solution. In order to prepare a biomaterial with the required characteristics, the control of the concentration of the precursor molecules before crosslinking is an important parameter. In order to retain this control, the dual compartment syringe comprises two compartments with a predefined volume ratio. Preferably the ratio of the volume of the compartments is 1:5 and more preferably 1:10. The larger compartment contains the mixture of the precursor molecules and the smaller compartment the basic solution. The dual compartment syringe is equipped with a detachable spray head and the content of the two compartments are sprayed together to form the biomaterial with a three dimensional network in situ at the site of need in the body.

DETAILED DESCRIPTION OF THE INVENTION

Definitions

Figure 1:
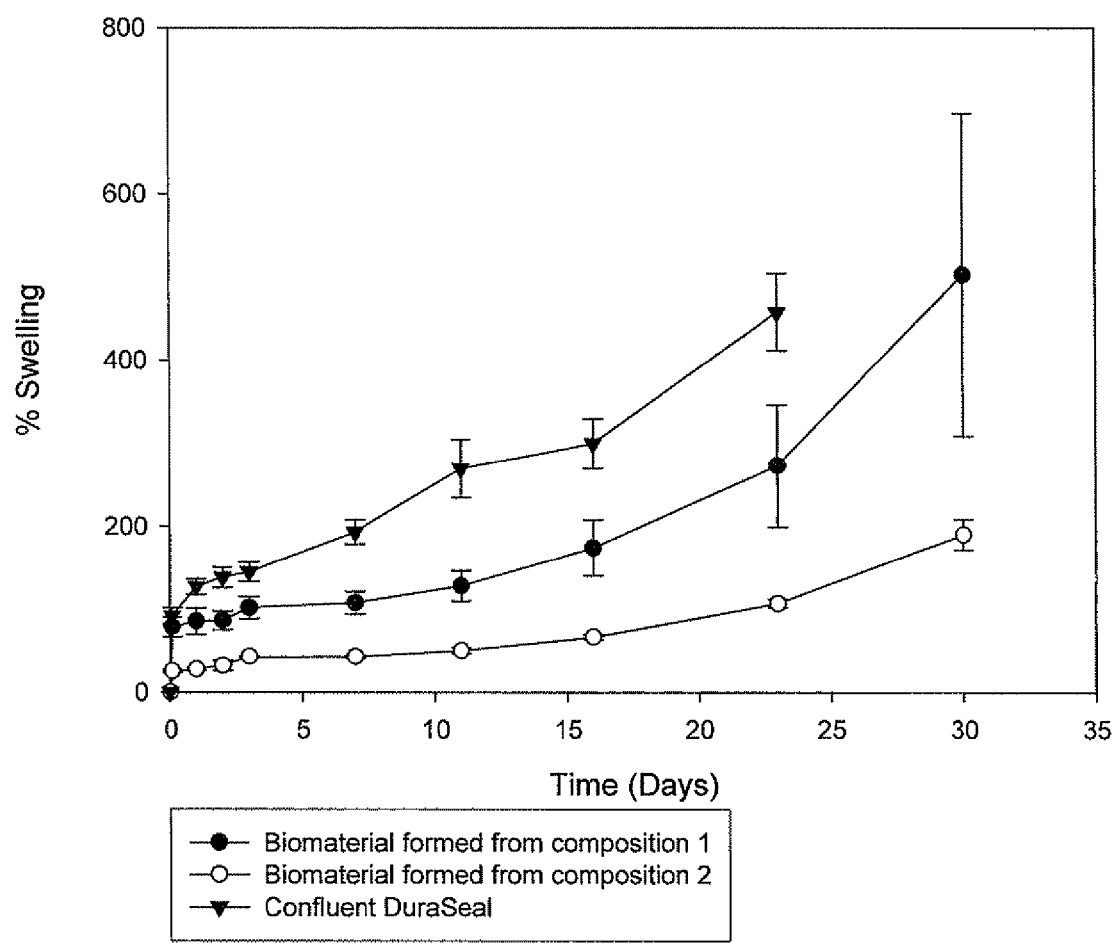
FIG. 1 shows a line graph of a comparison of percent swelling versus time (days) of representative formulations of the disclosed biomaterials and a commercially available biomaterial when stored in phosphate buffered saline at 37° C.

"Biocompatibility" or "biocompatible", as generally used herein, refers to the ability of a material to perform with an appropriate host response in a specific application. In the broadest sense, this means a lack of adverse effects to the body in a way that would outweigh the benefit of the material and/or treatment to the patient.

"Biomaterial" or "composition", as generally used herein, refers to a material intended to interface with biological systems to preferably evaluate, treat, or seal, any tissue, organ or function of the body. Biomaterial refers to the complete material (recursor molecules plus all additives, base or solvents and bioactive agents, if any) at and after having reached and passed its gel-point. "Composition" refers to the complete material before having reached its gel-point.

"Concentration of precursor components" as used herein refers to mass percent, being defined as the mass of the solute in grams multiplied by 100 divided by the mass of the overall solution in grams, (ie sum of solvent and solute): mass %=mass of solute (100)/mass of total solution.

"Conjugated unsaturated bond" can refer both to alternation of carbon-carbon, carbon-heteroatom or heteroatom-heteroatom multiple bonds with single bonds. Double bonds spaced by a $CH$ or $CH_2$ unit are referred to as "homoconjugated double bonds".

"Cross-linking" as generally used herein means the formation of covalent linkages. However, it may also refer to the formation of non-covalent linkages, such as ionic bonds, or combinations of covalent and non-covalent linkages.

"Crosslink density" as used herein means the average mass of polymer between crosslinks. Crosslink density is represented by the symbol $M_c$.

"Electrophilic group" as used herein, refers to functional groups which are capable of accepting an electron pair from a nucleophile in a polar-bond forming reaction. The terms electrophile and electrophilic groups are used synonymously.

"Functionality" as generally used herein means the number of reactive sites on a precursor molecule.

"Reactive sites" refer to nucleophilic and electrophilic groups that are able to react with each other at least, but not exclusively, under conditions in the human or animal body.

"Gel" refers to the state of matter between liquid and solid. As such, "a gel" has some of the properties of a liquid (i.e., the shape is resilient and deformable) and some of the properties of a solid (i.e., the shape is discrete enough to maintain three dimensions on a two dimensional surface).

"Gel point" as used herein refers to the point where the viscous modulus and elastic modulus cross each other and viscosity increases. Thus the gel point is the stage at which a liquid begins to take on the semisolid characteristics of a gel.

"In situ formation" as generally used herein refers to the ability of mixtures of precursor molecules which are substantially not crosslinked prior to and at the time of injection to form covalent or non covalent linkages with each other at a physiological temperature at the site of injection in the body.

"Molecular weight" as used herein refers to the weight average molecular weight of a number of molecules in any given sample, as commonly used in the art. Thus, a sample of PEG 5,000 might contain a statistical mixture of polymer molecules ranging in weight from, for example, 4,000 to 6,000 daltons (D) with one molecule differing slightly from the next over a range. Specification of a range of molecular weights indicates that the average molecular weight may be any value between the limits specified, and may include single molecules outside those limits. Thus, a molecular weight range of about 2,000 D to about 20,000 D indicates an average molecular weight of at least about 2,000 D, ranging up to about 20 kD.

"Multifunctional" as generally used herein means more than one functional group per precursor molecule.

"Nucleophilic group" as generally used herein refers to functional groups which are capable of donating an electron pair to an electrophile in a polar-bond forming reaction. Preferably the nucleophile is more nucleophilic than $H_2O$ at physiological pH. An example of a strong nucleophile is a thiol and refers to molecules which contain these functional groups. The terms nucleophile and nucleophilic group are used synonymously.

"Oligomer and polymers" are used in the usual sense of the terms. An oligomer is a low-molecular weight polymer. Oligomers typically contain between two and ten monomer units. As used herein, polymers typically contain more than 10 monomeric units.

"Poly(ethylene glycol) based polymer" refers to a polymer wherein the polymeric chain or chains of the polymer include poly(ethylene glycol).

"Physiological" as used herein means conditions as they can be found in living vertebrates. In particular, physiological conditions refer to the conditions in the human body such as temperature, pH, etc. Physiological temperature means generally a temperature range of between 35° C. to 42° C., preferably around 37° C. at atmospheric pressure. Physiological conditions can vary from one site in the body to another and/or due to the presence of disease, injury, or trauma.

"Polymeric network" as used herein refers to the product of a process in which substantially all of the monomers, oligomers, or polymers used as precursor molecules are bound by intermolecular linkages, preferably covalent ones, through their available functional groups to form a macromolecule.

"Precursor molecules" as used herein refers to molecules forming the polymeric network of the biomaterial. Other than the polymeric network the biomaterial can contain additives and biological active agents. Precursor molecules can be selected from functionalized monomers, oligomers and polymers.

"Respective counterpart" as used herein means the reaction partner of a given precursor molecule. The respective counterpart to the electrophilic group is the nucleophilic group and vice versa.

"Self selective reaction" as generally used herein means that the first precursor molecule of the composition reacts much faster with the second precursor molecule of the composition and vice versa than with other compounds present both in the composition and/or at the site of the reaction. As used herein, the nucleophilic group of the first precursor molecule preferentially binds to an electrophilic group of the second precursor molecule rather than to other biological compounds, and an electrophilic group of the second precursor molecule preferentially binds to the nucleophilic group of the first precursor molecule rather than to other biological compounds.

"Swelling" as used herein refers to the water uptake of the biomaterials. This is a function of the biomaterial mass increase at the equilibrium swelling, after placing the biomaterial in an excess of PBS buffer (10 mM phosphate buffered saline, e.g. P3813-powder from Sigma yields a buffer of 0.01 M phosphate, 0.0027 M potassium chloride and 0.138 M sodium chloride, pH 7.4) Typically the equilibrium swelling is reached within 2 days and is defined as the time when the biomaterial has reached its maximum mass before the biomaterial degrades. Swelling is measured by dividing the mass of the biomaterial at the equilibrium swelling by the initial mass of the biomaterial 10 min after the crosslinking reaction. The terms "water-uptake" and "swelling" are used synonymously throughout this application.

"Cohesive strength" refers to the ability of the biomaterials to remain intact, i.e., not rupture, tear or crack, when subjected to physical stresses or environmental conditions. "Cohesive strength" and "burst strength"" are used synonymously throughout this application.

"Adhesive strength" refers to the ability of the biomaterials to be able to remain attached to the tissues at the site of administration when subjected to physical stresses or environmental conditions.

I. Compositions

A composition for the manufacture of an in situ crosslinkable biomaterial which can be preferably used to reduce, prevent or contain fluid loss in the human body is provided. The composition contains at least a first and a second multifunctional precursor molecule. Optionally additives, colorants and/or biologically active agents may be added to the precursor molecules to form the composition. The composition comprises precursor molecules plus any additives and/or biological active agents. The precursor molecules can polymerize in situ at the site of need in the body to form the polymeric network of the biomaterial. The structure of the precursor molecules is selected based on the type of biomaterial that is desired.

A. Precursors

The first precursor molecule contains at least two nucleophilic groups, and the second precursor molecule contains at least two electrophilic groups. The first and second precursor molecules are selected such that the nucleophilic and electrophilic groups are capable of forming covalent linkages with each other under physiological conditions or under basic conditions. This can be achieved by different reaction mechanisms. One reaction mechanism is a nucleophilic substitution reaction. In another embodiment, the precursor molecules form covalent linkages via a Michael addition reaction between nucleophilic groups or moieties on the first precursor molecule and conjugated unsaturated groups or moieties on the second precursor molecule. The Michael addition reaction involves the reaction of a nucleophile, such as a thiol, amine, or hydroxyl group, with a conjugated unsaturated moiety, such as an α,β-unsaturated carbonyl-containing moiety.

Examples of precursor molecules include, but are not limited to, polyether derivatives, such as polyoxyalkylenes or derivatives thereof, peptides, and polypeptides, poly(vinyl pyrrolidinone) ("PVP"), and poly(amino acids). Preferred polyoxyalkylenes derivatives are polyethylene glycol ("PEG"), polypropylene oxide ("PPO"), polyethylene oxide ("PEO"), polyethylene oxide-co-polypropylene oxide ("PEO-PPO"), co-polyethylene oxide block or random copolymers, poloxamers, meroxapols, poloxamines and polyvinyl alcohol ("PVA"). Block copolymers or homopolymers (when A=B) may be linear (AB, ABA, ABABA or ABCBA type), star ($A_nB$ or $BA_nC$, where B is at least n-valent, and n is 3 to 6) or branched (multiple A's depending from one B). Preferred precursor molecules are selected from PEGs and PEO-PPO block copolymers. Most preferred PEGs and PEO-PPO block copolymers are applied in combination with each other. Preferably, the first precursor molecule is a poly(ethylene glycol) based polymer having x nucleophilic groups selected from the group consisting of thiol and amino groups, wherein x is greater than or equal to 2. Preferably, the first precursor molecule is of the general formula I:

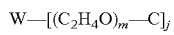  Formula I wherein m is an integer from 5 to 500;
j is equal to or greater than 2;
W is a branch point; and
C is a nucleophilic group.

Preferably, the branch point W of the first precursor molecule is selected from the group consisting of carbon, glycerol, pentaerythritol, dipentaerythritol and ethylene diamine. Preferably, C is an amino or a thiol group. More preferably, C is a thiol group. Preferably j equals 4. Preferably, W is pentaerythritol.

Preferably, the second precursor molecule is a multi arm poly(ethylene oxide-polypropylene oxide) (PEO-PPO) block copolymer of the general formula (II):

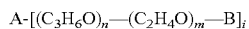  Formula II wherein m and n are integers from 1 to 200;
i is greater than 2;
A is a branch point; and
B is a conjugated unsaturated group.

The precursor molecules are multifunctional monomers, oligomers and/or polymers. Preferably the molecular weight of the first precursor molecule is in a range of between 2 to 20 kD, more preferably between 3 and 11 kD, most preferably between 5 and 10 kD. The preferred molecular weight of the second precursor molecule is between 10 and 25 kD, more preferably between 12 and 20 kD, most preferably between 14 and 18 kD.

Preferably, the branch point A of the second precursor molecule is selected from the group consisting of a methane derivative, glycerol, pentaerythritol, dipentaerythritol and ethylene diamine. In one embodiment, the biomaterial is formed from a multiarm arm poly(ethylene oxide-polypropylene oxide) (PEO-PPO) block copolymer of formula II, wherein A is an ethylene diamine molecule (i.e. that i equals 4) and B is and acrylate group (e.g., Tetronic®-tetraacrylate). Four-arm poly(ethylene oxide-polypropylene oxide) (PEO-PPO) block copolymer with an ethylene diamine core molecule are sold by BASF under the tradename Tetronic®. In a farther embodiment, the composition comprises a Tetronic® tetraacrylate having a molecular weight of about 15 kD (Tetronic® 1107) and a PEG tetrathiol with a molecular weight of about 10 kD. In another embodiment, the biomaterial is formed from a Tetronic® tetraacrylate having a molecular weight of about 15 kD and a PEG tetrathiol having a molecular weight of about 5 kD. In another preferred embodiment the biomaterial is formed from a Tetronic® tetraacrylate having a molecular weight of about 15 kD and a linear endfunctionalized PEG-dithiol of a molecular weight of about 3.4 kD. In still another embodiment the Tetronic® tetraacrylate is crosslinked with dithiothreitol (DTT).

Mechanical characteristics of the biomaterial (i.e., cohesive strength and adhesive strength, swelling and gelation time) are influenced by the number of arms of the precursor molecules and by the length of these arms. A high number of arms on each precursor molecule will result in a denser crosslinked network having a higher cohesive strength. However, the resorption of the resulting biomaterial will be longer. The chain length of the first precursor molecule has an influence on the swelling of the resulting biomaterial. Longer chains of poly(ethylene glycol) will provide a more swellable biomaterial compared to a biomaterial formed from precursor molecules with shorter chains of poly(ethylene glycol).

Preferably the precursor molecules are symmetrical, which means the branches have the same or nearly the same molecular weight and structure.

The sum of the functionality of the first and second precursor molecule is preferably greater than or equal to five. In one embodiment, the first precursor molecule has a functionality of four, and the second precursor molecule a functionality of three. In another embodiment, the first precursor molecule has a functionality of two, and the second precursor molecule a functionality of four. In still another embodiment one of the precursor molecules has a functionality of eight and the other of four. In still another embodiment, both precursor molecules have a functionality of four or more. A small and compact precursor molecule will form a polymeric network with greater strength than an extended precursor molecule, although the functionality and reaction partner might be the same for both molecules.

As a general guideline, the ratio of the first and second precursor components is selected such that the majority of the functional groups of both components react with the respective counterparts. The ratio of functional groups of the first and second precursor molecules (i.e., the ratio of electrophilic groups to nucleophilic groups is in the range of between 0.7 and 1.2, more preferably between 0.8 and 1.1 and most preferably 1 (i.e., stoichiometric ratio).

a. Nucleophilic Groups

The nucleophilic groups of the first precursor component are able to react with electrophilic groups, such as conjugated unsaturated groups in a variety of reaction mechanisms in a self-selective manner in the human body, through a nucleophilic substitution or Michael type addition reaction. The nucleophiles that are useful are those that are preferably reactive towards conjugated unsaturated groups via addition reactions, in particular in a self-selective Michael-type addition reaction under conditions in the human or animal body. The reactivity of the nucleophile depends on the nature of the nucleophile and the identity of the unsaturated group. The identity of the unsaturated group is first limited by its reaction with water at physiologic pH. Thus, suitable nucleophiles are generally more nucleophilic than water at physiologic pH. Suitable nucleophiles include, but are not limited to, —SH, —$NH_2$, —OH, —$PH_2$, and —CO—NH—$NH_2$ The usefulness of particular nucleophiles depends upon the situation envisioned and the amount of self-selectivity desired. In a preferred embodiment, the nucleophile is a thiol. However, amines and/or hydroxyl groups may also be effective nucleophiles.

Particular attention is paid to the pH, in that the deprotonated amine or thiol is a much stronger nucleophile than the protonated amine or thiol. As such, if particular attention is paid to the pK of an amine or thiol used as the strong nucleophile, substantial self-selectivity can be obtained. Reaction conditions where the pH of the solution is near the pK of the amines or thiols of the precursor molecules favor reaction of the conjugated unsaturated group with the amine or thiol provided, rather than with other nucleophiles present in the system.

The nucleophilic groups may be contained in molecules with great flexibility in overall structure. For example, a difunctional nucleophile could be presented in the form of Nuc-P-Nuc, where P indicates a monomer, oligomer or polymer and Nuc refers to the nucleophile. Likewise, a branched polymer, P, could be derivatized with a number of nucleophiles to create P-$(Nuc)_i$, where i is greater than 1. The nucleophile could be part of the repeating structure, e.g. (P-Nuc)$_i$. P and the nucleophile can be the same or different.

Polyethylene glycols and derivatives thereof can be chemically modified to contain multiple primary amino or thiol groups according to methods set forth, for example, in Chapter 22 of *Poly(ethylene glycol) Chemistry: Biotechnical and Biomedical Applications*, J. Milton Harris, ed., Plenum Press, NY (1992). In a most preferred embodiment the thiol present at the ends of the first precursor molecule is introduced on the PEG based polymers by substituting the terminal hydroxyl groups by a thiol group (SH). The precursor molecule thus obtained reacts faster with the second precursor molecule than a precursor molecule wherein the thiol group is introduced through a mercaptopropionate group.

Various forms of multi-amino PEG are commercially available from Nektar Therapeutics, Inc. of San Carlos, Calif. (through its acquisition of Shearwater Polymers of Huntsville, Ala.), and from Texaco Chemical Company of Houston, Tex. under the name "Jeffamine." Useful multi-amino PEGs include Texaco's Jeffamine diamines ("D" series) and triamines ("T" series), which contain two and three primary amino groups per molecule, respectively. Polyamines such as ethylenediamine ($H_2N$—$CH_2CH2$-$NH_2$)—, tetramethylenediamine ($H_2N$—$(CH_2)_{.5}$—$NH_2$), pentamethylenediamine (cadaverine) ($H_2N$—$(CH_2)_5$—$NH_2$)—, hexamethylenediamine ($H_2N$—$(CH2)_6$-$NH_2$), bis(2-hydroxyethyl)amine (HN—$(CH_2CH_2OH)_2$), bis(2-aminoethyl)amine (HN—$(CH_2CH_2NH_2)_2$), and tris(2-aminoethyl)amine (N—$(CH_2CH_2NH_2)_3$) may also be used as the synthetic polymer containing multiple nucleophilic groups.

Dithiothreitol (HS—$CH_2$—CHOH—CHOH—$CH_2$—SH) may also be used as the synthetic polymer containing multiple nucleophilic groups.

Preferred First Precursor Molecules

In a preferred embodiment, the first precursor molecule is a PEG tetra thiol according to formula III:

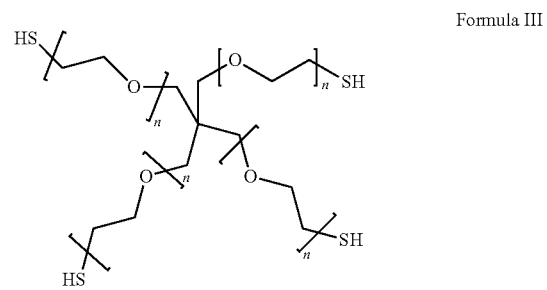

Formula III where n is in the range of between 25 and 60.

b. Electrophilic Groups

The electrophilic groups may be contained in molecules with great flexibility in overall structure. For example, a difunctional electrophile could be presented in the form of Elec-P-Elec, where P indicates a monomer, oligomer or polymer and Elec refers to the electrophile. Likewise, a branched polymer, P, could be derivatized with a number of electrophiles to create P-$(Elec)_i$, where i is greater than 1. The electrophile could be part of the repeating structure, e.g. (P-Elec)$_i$. P and the nucleophile can be the same or different. The electrophilic groups of the second precursor molecule are preferably conjugated unsaturated groups. It is only necessary that one electrophilic precursor contain greater than or equal to two such electrophilic groups.

It is possible to perform nucleophilic addition reactions, in particular Michael addition reactions, on a wide variety of conjugated unsaturated compounds. In the structures shown below, a monomeric, oligomeric or polymeric structure is indicated as P. Various preferred possibilities for the specific identity of P are discussed further herein. P can be coupled to reactive conjugated unsaturated groups, including but not limited to, those structures numbered 1 to 20 in Table 2.

TABLE 2

Molecular structures containing
P and conjugated unsaturated groups

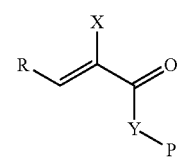

1a
X = H, $CH_3$, CN, COOW
R = H, W, Phenyl-(Ph)
Y = NH, O, 1,4-Ph
W = C1-C5 aliphatic chain TABLE 2-continued
Molecular structures containing P and conjugated unsaturated groups
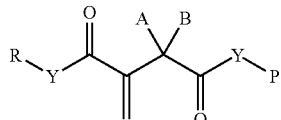
1b
A, B = H, alkyl
R = H, alkyl
Y = O, NH, 1,4-Ph
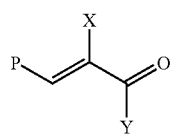
2
X = CN, COOW
Y = OW, Ph
W = C1-C5 aliphatic chain
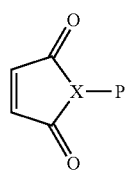
3
X = N, CH
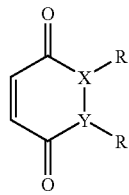
4
A X = CH Y = CH R = H, W-P (W = NH, O, nihil)
B X = N Y = N R = H, P
C X—Y = C≡C R = W-P (W = NH, O, nihil)
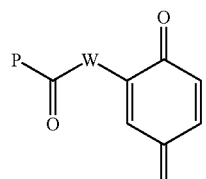
5
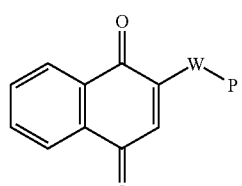
6
TABLE 2-continued
Molecular structures containing P and conjugated unsaturated groups
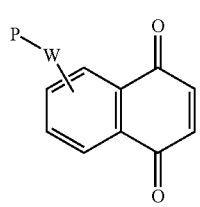
7
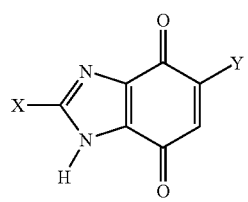
8
X, Y = H, P
P, P
P, H
P, aliphatic chain
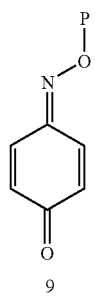
9
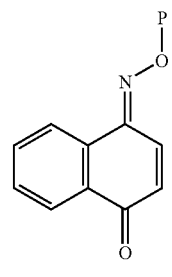
10
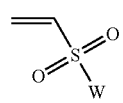
11
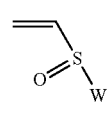
12

TABLE 2-continued

Molecular structures containing
P and conjugated unsaturated groups

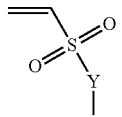

13

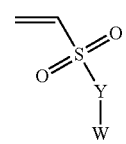

14
Y = O, NH
X = alkali or alkali earth
metal ion, P
W = P, 1,4-Ph-P

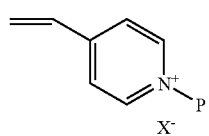

15
X = halogen, sulphonate

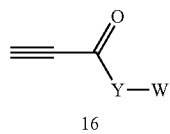

16

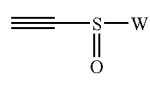

17

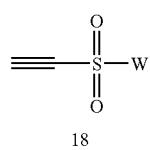

18

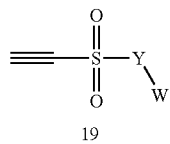

19

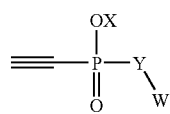

20
Y = O, NH
X = alkali or alkali earth
metal ion, P
W = P, 1,4-Ph-P

Reactive double bonds can be conjugated to one or more carbonyl groups in a linear ketone, ester or amide structure (1a, 1b, 2) or to two in a ring system, as in a maleic or paraquinoid derivatives (3, 4, 5, 6, 7, 8, 9, 10). In the latter case, the ring can be fused to give a naphthoquinone (6, 7, 10) or a 4,7-benzimidazoledione (8) and the carbonyl groups can be converted to an oxime (9, 10). The double bond can be conjugated to a heteroatom-heteroatom double bond, such as a sulfone (11), a sulfoxide (12), a sulfonate or a sulfonamide (13), or a phosphonate or phosphonamide (14). Finally, the double bond can be conjugated to an electron-poor aromatic system, such as a 4-vinylpirydinium ion (15). Triple bonds can be used in conjugation with carbonyl or heteroatom-based multiple bonds (16, 17, 18, 19, 20).

Structures such as 1a, 1b and 2 are based on the conjugation of a carbon-carbon double bond with one or two electron-withdrawing groups. One of them is always a carbonyl, increasing the reactivity passing from an amide, to an ester, and then to a phenone structure. The nucleophilic addition is easier upon decreasing the steric hindrance, or increasing the electron-withdrawing power in the alpha-position. For example, the following relationship exists, $CH_3<H<COOW<CN$, where $CH_3$ has the least electron-withdrawing power and CN has the most electron-withdrawing power.

The higher reactivity obtained by using the last two structures can be modulated by varying the bulkiness of the substituents in the beta-position, where the nucleophilic attack takes place; the reactivity decreases in the order P<W<Ph<H. Thus, the position of P can be used to tune the reactivity towards nucleophiles. This family of compounds includes some compounds for which a great deal is known about their toxicology and use in medicine. For example, water-soluble polymers with acrylates and methacrylates on their termini are polymerized (by free radical mechanisms) in vivo. Thus, acrylate and methacrylate-containing polymers have been used in the body in clinical products, but with a dramatically different chemical reaction scheme.

The structures 3-10 exhibit very high reactivity towards nucleophiles, due both to the cis configuration of the double bond and the presence of two electron-withdrawing groups. Unsaturated ketones react faster than amides or imides, due to the stronger electronegativity of these carbonyl groups. Thus, cyclopentendione derivatives react faster than maleimidic ones (3), and para-quinones react faster than maleic hydrazides (4) and cyclohexanones, due to more extended conjugation. The highest reactivity is shown by naphthoquinones (7). P can be placed in positions where it does not reduce the reactivity of the unsaturated group, that is in the opposite part of the ring (3, 5), on another ring (7, 8) or O-linked through a para-quinone mono-oxime (9, 10). To decrease the rate of the nucleophilic addition reaction, P can be also linked to the reactive double bond (6, 8).

The activation of double bonds to nucleophilic addition can be obtained by using heteroatom-based electron-withdrawing groups. In fact, heteroatom-containing analogues of ketones (11, 12), esters and amides (13, 14) provide similar electron-withdrawing behavior. The reactivity towards nucleophilic addition increases with electronegativity of the group. Thus the structures have the following relationship, 11>12>13>14, where 11 is the most electronegative and 14 is the least electronegative. The reactivity towards nucleophilic addition is also enhanced by the linkage with an aromatic ring. A strong activation of double bonds can also be obtained, using electron-withdrawing groups based on aromatic rings. Any aromatic structure containing a pyridinium-like cation (e.g., derivatives of quinoline, imidazole, pyrazine, pyrimidine, pyridazine, and similar $sp_2$-nitrogen containing compounds) strongly polarizes the double bond and makes possible quick Michael-type additions.

Carbon-carbon triple bonds conjugated with carbon- or heteroatom-based electron-withdrawing groups, can easily react with sulfur nucleophiles, to give products from simple and double addition. The reactivity is influenced by the substituents, in a manner similar to double bond-containing analogous compounds discussed above. In a preferred embodiment, the electrophilic groups are acrylate groups.

Preferred Second Precursor Molecules

In the preferred embodiment, the second precursor molecule is a monomer, oligomer or polymer that contains acrylates. In particular, the second precursor is a compound according to Formula IV:

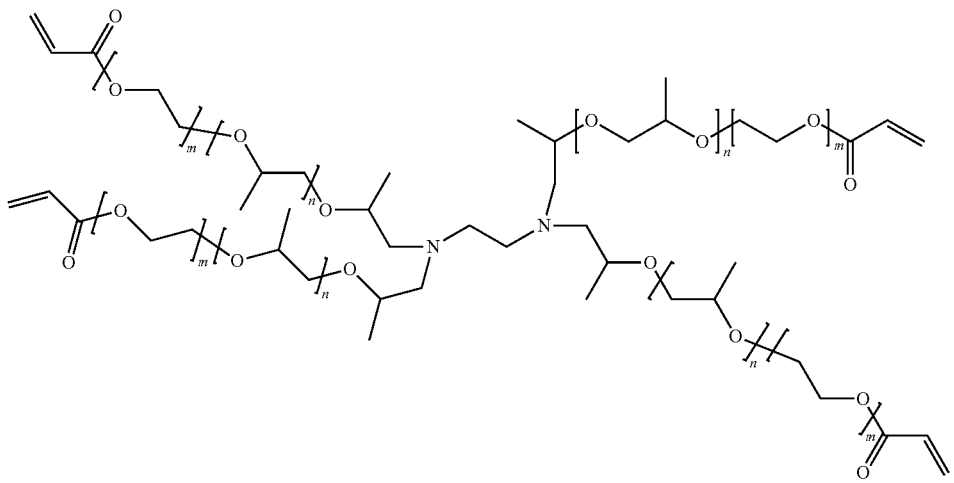

Formula IV where n and m are integers from 1 to 200.

Preferably, n is in a range of between 18 to 22 and m is in a range of between 58 to 62.

Tetronic® is a tetrafunctional block copolymer based on polyethylene oxide and polypropylene oxide available from BASF. Tetronic® block copolymers can be functionalized with conjugated unsaturated groups, such as acrylate groups, by reacting the free hydroxyl groups on the polymer with an excess of acryloyl chloride in the presence of a base. Other electrophilic group can be added in a similar manner.

c. Additives

The composition may further contain organic and/or inorganic additives, such as thixotropic agents, radiopaque agent and/or fluorescent agents in order to track the performance of application or to instantaneously detect potential leakage if not readily visible, stabilizers for stabilization of the precursor molecules in order to avoid premature polymerization and/or fillers which can result in an increase or improvement in the mechanical properties (e.g., ultimate compressive strength and Young's modulus E) of the biomaterial compared to the mechanical properties of the polymeric network. Examples of stabilizing agents include radical scavengers, such as butylated hydroxytoluene or dithiothreitol. Depending on the application, the composition (and thus biomaterial) may contain a colorant, preferably an organic color, such as a dye. In one embodiment methylene blue is added as a colorant. Methylene blue not only acts as a colorant but can also act as a stabilizer to the acrylate containing precursor molecules by acting as a reducing agent. It can also act as an indicator for disulfide formation (since it becomes colorless upon reduction). In another embodiment, fast green is added as a colorant. Another preferred colorant is lissamin green. Lissamin green and fast green are colorants which have the ability to change color due to the pH of the solution. They are green under acidic conditions and blue in basic conditions. Therefore, these two colorants have the additional advantage to indicate efficient mixing of the precursor molecule solutions with the basic solution.

d. Bases

The in situ crosslinking of the first and the second precursor molecules takes place under basic conditions. A variety of bases comply with the requirements of catalyzing the reaction under physiological conditions and of not being detrimental to the patient's body, thus acting as activators in the formation of the biomaterial Suitable bases include, but are not limited to, tertiary alkyl-amines, such as tributylamine, triethylamine, ethyldiisopropylamine, or N,N-dimethylbutylamine. For a given composition (and mainly dependent on the type of precursor molecules), the gelation time is dependant on the type of base and of the pH of the solution. Thus, the gelation time of the composition can be controlled and adjusted to the desired application by varying the pH of the basic solution. Increasing the pH of the basic solution will decrease the gelation time, but also will increase the degradation time of the biomaterial. Therefore, a compromise between gelation time and degradation has to be obtained. In a preferred embodiment the base, as the activator of the covalent crosslinking reaction, is selected from aqueous buffer solutions which have their pH and pK value in the same range. The pK range is preferably between 9 and 13. If the base has two pK values in the basic range, the first one is preferably between 8.5 and 10 and the second one is between 10 and 13. Suitable buffers include, but are not limited to, sodium carbonate, sodium borate and glycine. In one embodiment, the preferred base is sodium carbonate. Preferably the basic solution has a pH in a range of between 9 to 14, more preferably in a range of between 10 to 13 and even more preferably in a range of between 10 to 12.

e. Bioactive Agents

The biomaterial may also contain one or more bioactive agents, for example small molecules or peptides and proteins which can diffuse slowly from the biomaterial and thus helping the tissue to regenerate and heal. In such cases, the biomaterial works as both a tissue sealant with additional tissue regenerative properties and as a drug delivery matrix. The bioactive agents and/or small molecules can simply be mixed into the biomaterial or can be covalently bound to the biomaterial by incorporating a nucleophilic group, such as a free thiol group, into the molecule. The bioactive agent can be released by hydrolytic and/or enzymatic degradation. The bioactive factors may be growth factors, preferably those from the TGF beta superfamily and PDGF, variants thereof, or biologically active fragments thereof.

II. Biomaterials

As mentioned above, the requirements of biomaterials, and thus the choice of the precursor molecules, are dependent on the purpose and site of application in the body. In a preferred embodiment, the biomaterial forms a coating, a barrier or seal that prevents, reduces, or contains fluid loss. Fluid loss includes, but is not limited to the loss of any biological fluid or gas such as blood loss, cerebral spinal fluid loss or gas loss from lungs. The biomaterial can be applied internally or externally to the body. For this purpose, the biomaterial should have good adhesive and cohesive strength, an adaptable rapid gelation time, a low increase in volume due to water uptake, as well as complete resorption by the body over time. Whereas the mechanical stability of the biomaterial is essentially dependent on the crosslink density of the polymeric network, the water uptake by the biomaterial is influenced by interplay of the crosslink density, and the hydrophobicity of the polymeric network. Crosslink density and hydrophobic nature of the biomaterial are to a major extent determined by the structure and ratio of the precursor components. Therefore, water-uptake and mechanical performance of the biomaterial can be controlled and influenced by the appropriate choice of the precursor components.

Characteristics of the Biomaterials

In one embodiment, the biomaterial is used to seal the dura mater of the brain or spine after it has been cut or injured to prevent or reduce leakage of cerebrospinal fluid into the external environment following surgical intervention. The sealing can be done as a suture adjunct or if the damage to the dura mater is not too large. The biomaterial can be used as the only closure means to effect the non-surgical attachment of a first surface and a second surface. In the most preferred application, the composition is used as a suture adjunct to sutured dural repair after cranial surgery. One factor which influences the reaction time to form the biomaterial for use as a dural sealant (referred to as "sealant") is the pH of the composition at the time of crosslinking. The precursor molecules are dissolved in an aqueous buffer solution with a pH between 2 and 7.5, more preferably between 4 and 5. In a preferred embodiment sodium acetate with a pK of 4.76, sodium phosphate with a pK1 of 2.15 and a pK2 of 7.2 or hydrochloric acid (HCl) are employed to prepared the buffered solutions or to adjust the pH of the precursor molecule solutions. After or during mixture of the precursor molecules (and any additives and/or biologically active agents) an activator (e.g., base) is used to catalyze the reaction. Preferably a basic solution is used as an activator having at least one of its pK values in a range of between 9 and 13 is used as the activator. A preferred activator is sodium carbonate with a pK2 of 10.33 or sodium borate with pK1 of 9.23 and pK2 of 12.74. Additionally sodium borate has antiseptic properties and is also for this reason advantageously used for applications to wounds. In another embodiment glycine can be used as activator with a pK2 of 9.78. Preferably, the composition at the time of crosslinking has a pH in the range of between 9 to 13, preferably between 9.5 to 11.5, more preferably between 9.8 to 11, and most preferably between 10.3 to 10.6.

The composition used as a dural sealant should have a very quick crosslinking time in order to stay in place and immediately prevents leakage. The composition crosslinks in less than two minutes, preferably in less than one minute, more preferably between 5 and 20 seconds, most preferably between 1 and 5 seconds.

The swelling of the biomaterial should be limited since swelling might result in pressure on tissues resulting in nerve compression or ischemia. As defined herein before, the swelling of the sealant should not exceed 1.5 and preferably is less than 1, more preferably less than 0.5 In a preferred embodiment, the swelling is between 0.1 to 1.5, preferably between 0.1 to 1, more preferably 0.1 to 0.8. In a preferred embodiment at least one of the precursor molecules has as the backbone a molecule more hydrophobic than polyethylene glycol. For example, in one embodiment, the first precursor molecule has a PEG backbone in combination with a PEO/PPO block copolymer as the backbone of the second precursor molecule. Preferably both of the precursor molecules have a number of end-functionalized arms of three or more. Most preferably both precursor molecules contain four end-functionalized arms. Preferably the first precursor molecule is a PEG tetrathiol (Formula III) having a molecular weight between 4 kD and 11 kD more preferably between 5 kD and 10 kD. The second precursor component preferably is a Tetronic® tetraacrylate (Formula IV) having a molecular weight in between 10 kD and 20 kD, more preferably of about 15 kD. In particular good properties of a sealant material can be achieved by combining a 5 kD or 10 kD PEG tetrathiol with a Tetronic® tetraacrylate. The concentration of the second precursor molecule (the electrophilic precursor) forming the biomaterial is in a range of between 8% to 18% w/w, more preferably between 10% to 16% w/w and most preferably between 12% and 14% w/w. The concentration of the first precursor molecule (nucleophilic precursor molecule) is calculated and adjusted according to the desired ratio of functional groups between first and second precursor molecules. The concentration ranges of the precursor molecules have also a significant impact on swelling, gelation and resorption time of the biomaterial and for this reason the optimal range is of importance for the ultimate properties as a sealant. Starting with a low concentration of the precursor molecules will increase the gelation time but will result in a biomaterial that will swell to a lower extent. In a preferred embodiment, the biomaterial degrades in vivo in less than 12 weeks.

III. Methods of Forming Biomaterials

A. Storage

The first and second precursor molecules are preferably stored in solution under exclusion of oxygen and at low temperatures, e.g. around +4° C., to avoid decomposition of the functional groups prior to use. The precursor molecules can be stored as a dry powder or as a solution in a buffer. In one embodiment, the two precursor molecules are stored as a solution in an acidic sodium acetate buffer. In another embodiment the first precursor molecule is stored as a dry powder and the second precursor molecule is stored in a solution having an acidic pH.

B. Preparation of Composition for Tissue Sealant

A composition for forming a biomaterial, in particular a tissue sealant may be prepared by the following general method:

a) providing at least one first multifunctional precursor molecule containing at least two nucleophilic groups, preferably four nucleophilic groups, which optionally comprises additives and/or biologically active agents;

b) providing at least one second multifunctional precursor molecule containing at least two electrophilic groups, preferably four electrophilic groups capable of forming covalent linkage with the nucleophilic groups of step a) under physiological conditions, which optionally comprises additives and or biologically active agents;

c) dissolving the precursor molecules of step a) and b) in a buffer solution, preferably having an acidic pH;

d) mixing the precursor molecule solutions obtained in step c); and e) adding an basic solution during step d) or thereafter, preferably an aqueous buffer solution with a pH value in between 9 and 13 to initialize the crosslinking reaction between the first and second precursor molecule solutions.

In a preferred embodiment, a method for making a biomaterial includes the steps of:

i) providing a first precursor molecule which is a poly(ethylene glycol) based polymer having x terminal thiol groups, wherein x is greater than or equal to 2;

ii) providing a second precursor molecule of the general formula:

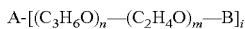

$$A\text{-}[(C_3H_6O)_n\text{—}(C_2H_4O)_m\text{—}B]_i$$

wherein m and n are integers from 1 to 200;
i is greater than 2;
A is selected from the group consisting of carbon, glycerol, pentaerythritol, dipentaerythritol and ethylene diamine;
B is a conjugated unsaturated group;
wherein m and n are integers from 1 to 200; and iii) reacting precursor molecules of steps i) and ii) in the presence of a base to form a crosslinked three dimensional network.

When the first and second precursor molecules are mixed crosslinking occurs with a slow rate (from 10 minutes to hours) if the pH of the solution is acidic. In order to avoid the mixture reaching the gelation point before administration and to form the biomaterial in a rapid predefined time, the precursor molecules should be stored in solution having an acidic pH. Preferably, the pH of the solution in a range of between 2 to 6 and more preferably in a range between 2.5 to 5.5. Preferred acidic solution are obtained with an acetate buffer or a hydrochloric acid solution.

In a preferred embodiment, the first and second precursor molecules are dissolved in a buffer solution having an acidic pH. In another preferred embodiment, the first precursor molecule is a dry powder, the second precursor molecule is dissolved in a buffer solution having an acidic pH and the two precursor molecules are mixed prior to be in contact with the base. The first and second precursor molecules and any additives and/or biologically active agents, if present, can optionally be sterilized prior to mixing. This preferably is done by sterile filtration of the precursor components and any soluble other component and by gamma irradiation of water insoluble components. The precursor molecules obtained in steps a), b) and/or the mixture obtained in step d) can be stored over a prolonged time, preferably at low temperatures. Prior to application, the precursor molecules (and other components, if present) are mixed with one another and subsequently with a basic solution as activator. Upon introduction of the basic solution, the composition rapidly gels. Preferably, the composition, including the basic solution, has a pH in a range of between 9 to 13, more preferably in a range of between 9.5 to 11.5, even more preferably in a range of between 9.8 to 11 and even more preferably in a range of between 10.3 to 10.6 to allow gelation to occur in less than 2 minutes, preferably in less than 10 seconds and more preferably in less than 5 seconds.

Mixing can be achieved using a variety of techniques. In one embodiment, three syringes, one containing the nucleophilic precursor, another containing the electrophilic precursor, and the third containing the basic solution, can be interconnected using a three-way connector device. The contents of the syringes are mixed by being squeezed through a static mixture at the outlet of the three way connector device. The composition is injected directly at a site in need of treatment in the body by connecting the static mixer to an injection needle. In a second embodiment, one of the precursor molecule solutions is mixed with the basic solution. This is preferably done by connecting the syringe containing the basic solution to the syringe preferably containing the electrophilic precursor (optionally also containing additives and/or biological active agents) through a connector device, which allows for syringe-to-syringe mixing of the respective contents. A static mixer may be part of the connector device. The mixing is complete when homogenous mixing is achieved. After mixing, one syringe contains a mixture of the base/precursor molecule and the other syringe is empty. Then, the empty syringe is removed from the connector device and replaced by the syringe containing the other precursor molecule optionally also containing additives and/or biological active agents. Again, syringe-to-syringe mixing is one way to achieve homogeneous mixing of both contents. Subsequently the syringe containing the mixture is connected to the injection needle and the composition is injected at the site of need in the body.

Alternatively, the syringe containing the base/precursor mixture and the syringe containing the other precursor are interconnected through a two-way connector device comprising a static mixer at its outlet. The two-way connector device can be a double compartment syringe. The contents are mixed by squeezing the contents of the syringes through the static mixer. The static mixture is either directly connected to the injection needle or the mixture is squeezed in a further syringe, which then is connected to the injection needle.

In a preferred embodiment, the first and second precursor molecule solutions, preferably first and second precursor molecules dissolved in a sodium acetate buffer, are mixed (together with any additives or biologically active agents, if needed) and then sprayed together with an activator, a basic solution, onto the tissue.

IV. Kits for Forming In Situ Crosslinkable Compositions

The kits are a set of parts used for forming the disclosed biomaterials. The kit contains at least a first and a second precursor component. The kit may also contain one or more devices, such as syringes or dual compartment syringes, for administering the first and second precursor molecules plus any additives and/or biologically active agents. The kit may also contain containers to store the precursor molecules and the basic solution, such as vials. The kits also contain needle-free devices to transfer the contents of the containers into each other or to transfer the contents of the containers into a dual compartment syringe. Optionally, the kit also contains a basic solution. Preferably, the base is stored in a third container. Optionally, the first and/or the second precursor molecules contain one or more additives and/or biologically active agents. The precursor molecules may be placed in the one or more devices prior to administration to a patient. The kit can also include a dye, for example methylene blue, lissamin green or fast green, that can be added to the biomaterial to facilitate visualizing the biomaterial. In a preferred embodiment, the precursor molecule solutions are stored in each of the compartments of a dual compartment device and the basic solution is stored in the second compartment of the same device. The outlet of the device contains a spraying nozzle which optionally can be combined with a static mixer to optimize the mixing of the basic solution with the precursor molecule solutions. The precursor molecule solutions (plus any additives or biological active agents if necessary) can be contained in the compartment premixed or the precursor molecules can be separated in the compartment by a membrane which allows mixing of the molecules upon removal or destruction of the membrane.

In another embodiment, the kit comprises a first container (under vacuum), which can be a glass vial, containing the first precursor molecule as a dry powder and a second container, which can be a glass vial, containing the second precursor molecule dissolved in an aqueous buffered solution having an acidic pH. Optionally, the first or second container may contain one or more additives selected from the group consisting of thixotropic agents, radiopaque agents, and colorants. The content of the second container is transferred into the first container via a needle-free transfer device (Mix2Vial® 20/20, West). (Thereafter the first and second precursor molecules are mixed and dissolved in an aqueous buffered solution having an acidic pH). A third container, which can be a glass vial, comprises the basic solution. A dual compartment syringe is equipped with a double filing adaptor. The two compartments of the dual syringe may have a different volume. Preferably, the volume of the compartment receiving the mixture of the precursor molecules is ten times higher than the volume of the compartment receiving the basic solution. The container containing the precursor molecules and the container containing the base are connected to a connecting means and their contents are simultaneously transferred into the two compartments of the syringe by pulling on the pistons of the syringe. The connecting means and the two containers are removed from the syringe and the syringe is equipped with a detachable spray nozzle. The mixing of the precursor molecules solution and the basic solution occurs in the spray nozzle and the resulting intimate mixture is sprayed at the desired site.

V. Uses for the Compositions

The multifunctional precursor components are selected and tailored to produce biomaterials with the desired properties. The precursor molecules are capable of in situ crosslinking under physiological conditions (e.g., temperature) to specific sealant requirements. In the preferred embodiment, the compositions and biomaterials are used to prevent, reduce, inhibit or contain loss of biological fluids. In another embodiment, the compositions and biomaterials are used for coating the surface of a tissue.

A. Tissue Sealant

In one embodiment, the compositions and biomaterials are used as tissue sealants. In the preferred embodiment, the in situ crosslinkable composition forms a biomaterial forming a coating, a barrier or a sealant to reduce, inhibit, or contain fluid loss. In particular, the biomaterial may be used to inhibit, reduce, or contain fluid loss after a medical procedure. A preferred medical procedure includes, but is not limited to brain or neurosurgical surgery.

B. Medical Indications Other than Tissue Sealant.

The disclosed biomaterials are not limited for use in surgical procedures. The biomaterial can be used as a wound dressing for a wound on any body part. In one embodiment, the biomaterial can be used as a field dressing to prevent or reduce blood loss resulting from trauma. In another embodiment the biomaterial can be used to reduce or prevent post-surgical anti-adhesion.

EXAMPLES

Materials

Ethylene diamine tetrakis(poly(ethylene oxide-propylene oxide) block copolymers) (Tetronic® 1107 mol. wt. 15 kD, BASF) were end-functionalized with acrylate groups to form ethylene diamine tetrakis((poly(ethylene oxide-propylene oxide) block copolymers)-acrylate) (tetronic-tetraacrylate, mol. wt-15 kD) according to the method described in Biomaterials 25 (2004) 5115-5124.

Buffer Preparation 0.3 M Triethanolamine (TEA) was prepared by dissolving 1.11 g triethanolamine in 25 ml of Milli-Q water and adjusting the pH by addition of 5 M hydrochloric acid.

TBS was prepared by dissolving 8 g NaCl, 0.2 g KCl and 3 g Tris base in 1 l of MilliQ-water. The pH was adjusted with 5 M NaOH.

Glycine Buffer: 7.5 g Glycine and 5.85 g NaCl were dissolved in 1 l MilliQ-water. The pH was adjusted with 5 M NaOH.

Acetate buffer: A 10 mM acidic acid and a 10 mM sodium acetate buffer were prepared with MilliQ-water. The two buffers were mixed in a ratio to obtain the desired pH.

Borate buffer: A 100 mM boric acid buffer and a 50 mM sodium tetraborate decahydrate buffer were prepared. The two buffers were mixed in a ratio to obtain a desired pH.

Carbonate buffer: A 100 mM sodium carbonate buffer and a 100 mM sodium bicarbonate buffer were prepared in MilliQ-water. The two solutions were mixed in a ratio to obtain the desired pH.

Gelation Test

To assess the gelation time, 50-100 µl of of the first precursor molecule solution and the second precursor molecule solution from Table 2 where pipetted into Eppendorf® tubes. For the fast gelling materials, the drops (of equal volume) of the respective first precursor molecule solution were placed on the inner wall to prevent premature gelation before coming in contact with the second precursor solution. A timer was started simultaneously with placing the Eppendorf® ion a vortex, where the solutions were as then mixed for exactly 5 seconds. Immediately after the mixing, the combined solutions were was probed with a needle and the "gel point" (defined as the time at which when thin threads remained attached to the needle after withdrawal) was recorded. For fast gelling formulations the status after probing at 5 seconds was recorded (e.g., thin threads, thick threads and/or hard gel). Alternatively, mixing was performed by syringe to syringe mixing. For this, the first precursor molecule solution and the second precursor molecule solution were taken up into syringes, the syringes were connected with a coupler and the solution was pushed back and forward ten times. The mixture was transferred into a weighing dish and the gel point was determined as described above by "needle-probing". After initial gelling, the hydrogel typically remained sticky until a major degree of cross-linking was achieved. The time the material needed to sufficiently cross-link (loss of sticky character) was recorded as "set time" which reflects the time after which the material can be touched without damage.

Example 1

Tissue Sealant Compositions

1a. Composition 1: Tetronic-Tetraacrylate and PEG-SH-10
First Precursor Molecule Solution 235 mg of poly(ethylene glycol) tetrasulfhydryl ("PEG-SH-10") (mol. wt. 10 kD) and 0.1 mg of lissamin green were dissolved in 1 mL of 10 mM acetate buffer pH 5.

Second Precursor Molecule Solution 315 mg of tetronic-tetraacrylate (mol wt. 15 kD) were dissolved in 1 mL of a 10 mM acetate buffer pH 5.

Basic Solution 0.22 mL of a 50 mM borate buffer pH 9.8
1b: Composition 2: Tetronic-Tetraacrylate and PEG-SH-5
First Precursor Molecule Solution
 112 mg of poly(ethylene glycol) tetrasulfhydryl ("PEG-SH-5") (mol. wt. 5 kD) and 0.1 mg of lissamin green were dissolved in 1 mL of 10 mM acetate buffer pH 5.
Second Precursor Molecule Solution
 315 mg of tetronic-tetraacrylate (mol wt. 15 kD) were dissolved in 1 mL of a 10 mM acetate buffer pH 5.
Basic Solution
 0.22 mL of a 50 mM borate buffer pH 10.4
1c: Composition 3: Tetronic-Tetraacrylate and PEG-SH-5
First Precursor Molecule Solution
 168 mg of poly(ethylene glycol) tetrasulfhydryl ("PEG-SH-5") (mol. wt. 5 kD) were dissolved in 1 mL of 10 mM acetate buffer pH 4.9.
Second Precursor Molecule Solution
 472 mg of tetronic-tetraacrylate (mol. wt. 15 kD) were dissolved in 2 mL of a 20 mM acetate buffer pH 4.9.
Basic Solution
 0.3 mL of a 250 mM carbonate buffer pH 11.0
1d: Composition 4: Tetronic-Tetraacrylate and PEG-SH-5
First Precursor Molecule Solution
 192 mg of poly(ethylene glycol) tetrasulfhydryl ("PEG-SH-5") (mol wt. 5 kD) were dissolved in 1 mL of 5 mM acetate buffer pH 4.9.
Second Precursor Molecule Solution
 472 mg of tetronic-tetraacrylate (mol. wt. 15 kD) were dissolved in 1 mL of a 15 mM acetate buffer pH 4.9.
Basic Solution
 0.3 mL of a 250 mM carbonate buffer pH 11.0
1e. Composition 5: Tetronic-Tetraacrylate and DTT
First Precursor Molecule Solution
 2.5 mg of dithiothreitol (DTT, mol. wt. 154 g/mol) was dissolved in 500 μL of a 0.3 M triethanolamine buffer at pH 8.5.
Second Precursor Molecule Solution
 120 mg of tetronic-tetraacrylate (mol. wt. 15 kD) was dissolved in 500 μL of a 0.3 M triethanolamine buffer at pH 8.5.
Or
First Precursor Molecule Solution
 3.15 mg of dithiothreitol was dissolved in 500 μL of a 0.3 M triethanolamine buffer at pH 8.5.
Second Precursor Molecule Solution
 150 mg of tetronic-tetraacrylate (mol. wt. 15 kD) was dissolved in 500 μL of a 0.3 M triethanolamine buffer at pH 8.5.
1f. Composition 6: Tetronic-Tetraacrylate and 2 Arm PEG-SH-3.4
First Precursor Molecule Solution
 156 mg of poly(ethylene glycol) disulfhydryl ("PEG-SH-3.4") (mol. wt. 3.4 kD) was dissolved in 1 mL of 10 mM acetate buffer pH 5.5.
Second Precursor Molecule Solution
 315 mg of tetronic-tetraacrylate (mol wt. 15 kD) was dissolved in 1 mL of a 10 mM acetate buffer pH 5.5.
Basic Solution
 0.3 mL of a 250 mM carbonate buffer pH 10.0
1g. Composition 7: Tetronic-Tetraacrylate and 8 Arm PEG-SH-10
First Precursor Molecule Solution
 161 mg of 8 arm poly(ethylene glycol) octasulfhydryl ("8 arm PEG-SH-10") (mol. wt. 5 kD) was dissolved in 1 ml of 10 mM acetate of pH 4.9.

Second Precursor Molecule
 472 mg tetronic-tetraacrylate (15 kD) was dissolved in 2 ml of 20 mM acetate of pH 4.9.
Basic Solution
 0.3 mL of 0.25 M sodium carbonate buffer at pH 11.0
1h. Composition 8: Tetronic-Tetraacrylate and 4 Arm PEG-SR-5
 472 mg of Tetronic-tetraacrylate, 15 kD
 192 mg PEG-tetrathiol, 5 kD
 0.55 mg Hydrochloric acid
 9.5 mg Sodium carbonate
 0.15 mg Methylene blue hydrate
 3.3 g water for injection
Preparation of the Kit:
 HCl stock solution, 5 mM were prepared by diluting 5 ml of 100 mM HCl solution in 95 ml milli-Q-water. Methylene blue stock solution, 1 mg/ml in 5 mM HCl was prepared by dissolving 20 mg of methylene blue in 20 ml of HCl stock solution.
 Buffer for tetronic-tetraacrylate reconstitution was prepared from 5 mM HCl with 0.05 mg/ml methylene blue. It was diluted with HCl stock solution at a ratio of 1:20, pH was adjusted to be within the range 2.3-2.6. pH of the basic solution (carbonate buffer) was adjusted to be within the range 11.35-11.45.
 472 mg of tetronic-tetraacrylate was dissolved in 3 ml cold Buffer tetronic tetraacrylate and kept on ice for 5 minutes to ease solubilization. The solution was centrifuged for 1 minute at 3000 rpm to remove air-bubbles and pipetted into a vial containing 192 mg PEG-tetrathiol which was dissolved by gentle shaking. After polymer reconstitution, the mixture 3 ml was transferred into the larger compartment of a 1:10 double syringe. The smaller compartment was filled with 0.4 ml 300 mM sodium carbonate. The plunger was inserted, air was carefully removed from the syringe and the spray nozzle attached.
1i. Preparation of DuraSeal®
 DuraSeal® (Confluent Surgical Inc.) was prepared according to the instructions for use.
1j. Composition 10 Tetronic-Tetraacrylate and 2 Arm PEG-SH-3.4
 133 mg of poly(ethylene glycol) disulfhydryl ("PEG-SH-3.4") (mol. wt. 3.4 kD) was dissolved in 500 μL of a 0.3 M triethanolamine buffer at pH 8.5.
Second Precursor Molecule Solution
 220 mg of tetronic-tetraacrylate (mol. wt. 15 kD) was dissolved in 500 μL of a 0.3 M triethanolamine buffer at pH 8.5.
1k. Composition 11: Tetronic-Tetraacrylate and 2 Arm PEG-SH-3.4
 107 mg of poly(ethylene glycol) disulfhydryl ("PEG-SH-3.4") (mol. wt. 3.4 kD) was dissolved in 1.5 mL of a 0.3 M triethanolamine buffer at pH 8.5.
Second Precursor Molecule Solution
 220 mg of tetronic-tetraacrylate (mol. wt. 15 kD) was dissolved in 500 μL of a 0.3 M triethanolamine buffer at pH 8.5.
1l. Composition 12: Tetronic-Tetraacrylate and 2 Arm PEG-SH-3.4
 354 mg of poly(ethylene glycol) disulfhydryl ("PEG-SH-3.4") (mol. wt. 3.4 kD) was dissolved in 1.5 mL of a 0.3 M triethanolamine buffer at pH 8.5.
Second Precursor Molecule Solution
 240 mg of tetronic-tetraacrylate (mol. wt. 15 kD) was dissolved in 500 μL of a 0.3 M triethanolamine buffer at pH 8.5.

1m. Composition 13: Tetronic-Tetraacrylate and 2 Arm PEG-SH-3.4

140.7 mg of poly(ethylene glycol) disulfhydryl ("PEG-SH-3.4") (mol. wt. 3.4 kD) was dissolved in 50 µL of a 100 mM borate buffer at pH 10.1, 9.8 and 9.6.

Second Precursor Molecule Solution 286 mg of tetronic-tetraacrylate (mol. wt. 15 kD) is 50 µL of a 100 mM borate buffer at pH 8.5.

Example 2

Preparation of the Biomaterial

2a. Preparation of the Biomaterial from Composition 1, 2, 3, 4 and 6

Before application of the pharmaceutical composition at the desired site, the first and second precursor molecule solutions were filled into two distinct syringes, which were connected with a coupler. The first and second precursor molecule solutions were mixed by transferring the material contained in one syringe to the other syringe (Typically, the solutions were pushed back and forward 10 times). Although, the mixture typically remains stable 10-20 minutes after its preparation, ideally the pharmaceutical composition should be used within 5 minutes after its preparation. The biomaterial was formed in situ at the desired site, by delivering to the defect site the mixture comprising the first and second precursor molecules and the activator using a two component device equipped either with a spreader tip or a sprayer tip. The biomaterial was formed in less than 1 minute after delivery of the content of the two component device.

2b. Preparation of the Biomaterial from Composition 5, 10, 11, 12 and 13

The first and second precursor molecule solutions were filled into two distinct syringes which were connected with a coupler. The first and second precursor molecule solutions were mixed by transferring the material contained in one syringe to the other syringe. The gelation point was reached in the syringe and the biomaterial was extruded from the syringe and delivered into a mold.

2c. Preparation of the Biomaterial from Composition 7

The two precursor molecules were mixed by syringe-to-syringe mixing. Without addition of a basic solution, the precursor molecules gelled within 30 min. This means that the mixture of the precursor molecules can be stored for 30 minutes before use. When 300 µl of 0.25 M sodium carbonate buffer at pH 11.0 were added, the gelation occurred in few seconds (less than 5 seconds).

Example 3

Stability of the Mixture of the First and Second Precursor Molecules

First Precursor Molecule Solution 194 mg of poly(ethylene glycol) tetrasulfhydryl ("PEG-SH-5") (mol. wt. 5 kD) were dissolved in 1 mL of 10 mM acetate buffer pH 4.9. The buffer was prepared by mixing a 100 mM acetic acid buffer and a 100 mM sodium acetate buffer to achieve pH 4.90 and diluting the buffer 1:10 v/v with water.

Second Precursor Molecule Solution 545 mg of tetronic-tetraacrylate (mol wt. 15 kD) were dissolved in 2 mL of a 20 mM acetate buffer pH 4.9. The buffer was prepared by mixing a 100 mM acetic acid and a 100 mM sodium acetate buffer to achieve pH 4.90 and diluting the buffer 1:5 v/v with water.

Basic Solution 0.3 mL of a 250 mM Carbonate Buffer pH 11.0

When only the first and second precursor molecules were mixed by vortexing 30 s, gelation was occurring within 30 min. Gelation time was measured by dipping a needle in and out of the solution, the time was measured until threads were formed indicating an advanced degree of cross-linking of the material. At a lower concentration of precursor molecules, i.e. for precursor molecule solutions prepared as described in example 1c and 1d (composition 3 and composition 4), gelation only occurred after 1 h. When the basic solution was applied to the mixture of precursor molecules, both compositions gelled within seconds (in less than 10 seconds).

Example 4

Effect of the Ratio Between the Number of Acrylates and Thiols Functional Groups Present in the Corresponding Polymers The first precursor molecule solution and the second precursor molecule solution as defined in example 1c were mixed in different volume ratios (0.25:1, 0.375:1, 0.5:1, 0.675:1 and 0.75:1). These ratios correspond to molar thiol to molar acrylate ratios of 10.5, 1:0.75, 1:1, 1:1.25 and 1:1.5. The first precursor molecule solution and the second precursor molecule solution were mixed for 30 seconds by vortexing. 0.2 mL of a 50 mM borate buffer pH 9.3 was then added in a volume corresponding to one tenth of the total volume of the precursor molecule solutions. The mixture was mixed by vortexing for 5 seconds. By dipping a needle in and out of the solution, the time was measured until threads were formed indicating an advanced degree of cross-linking of the material. A minimum gelation time of 10-11 seconds was obtained for the samples with a molar ratio of acrylate to thiol of 1:1 and 1:0.75. The gelation time increased to 13-15 seconds for the other ratios.

Example 5

Swelling/Degradation of the Biomaterial

To assess the swelling and degradation of the biomaterial, biomaterials were prepared from compositions as described in examples 1a and 1b.

Figure 2:
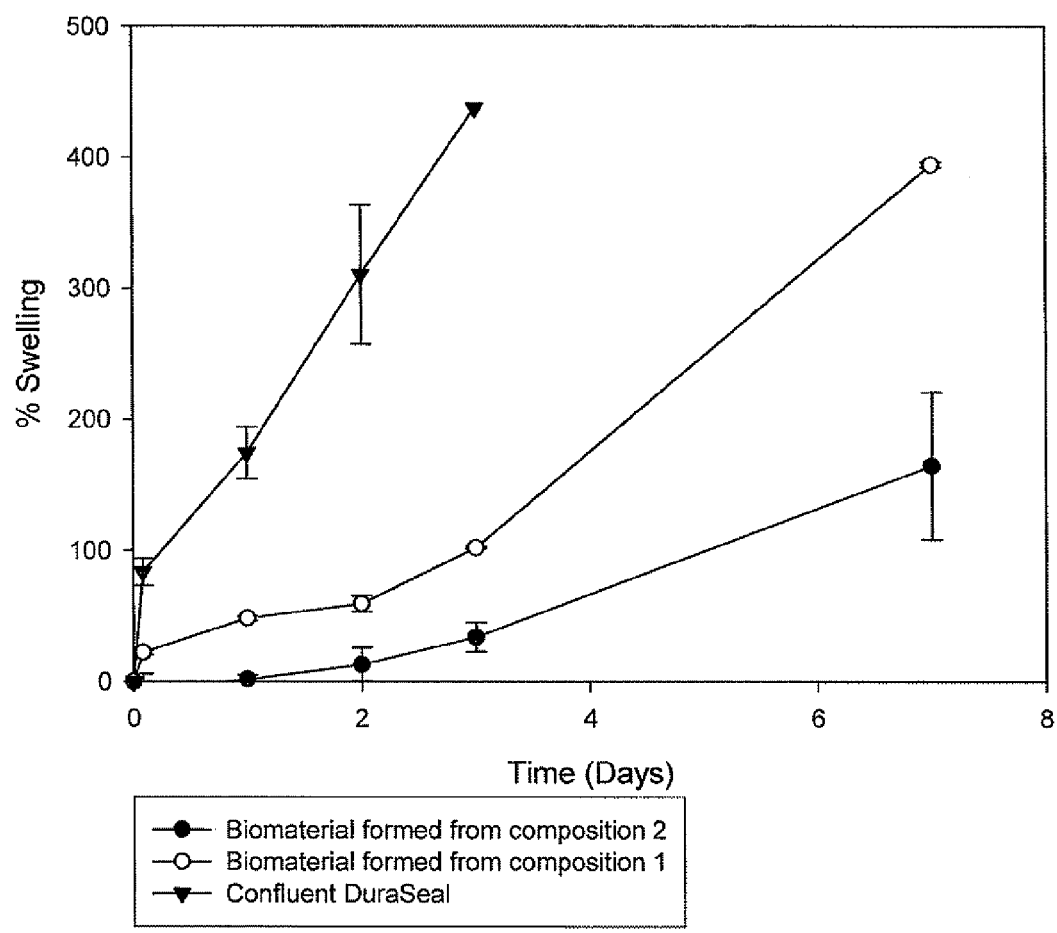
FIG. 2 shows a line graph of a comparison of percent swelling versus time (days) of representative formulations of the disclosed biomaterials and a commercially available biomaterial when stored in phosphate buffered saline at 50° C.

Before application of the compositions at the desired site, the first and second precursor molecule solutions were filled into two distinct syringes which were connected with a coupler. The first and second precursor molecule solutions were mixed by transferring the material contained in one syringe to the other syringe (Typically, the solutions were pushed back and forward 10 times). Although, the mixture remained stable 10-20 minutes after its preparation (meaning that the mixtures have not reached the gelation point before 10 to 20 minutes), the compositions should ideally be used within 5 minutes after its preparation. The biomaterials were formed in situ at the desired site, by delivering to desired site the mixtures comprising the first and second precursor molecules and the basic solution using a two compartment device equipped either with a spreader tip or a sprayer tip. The biomaterials were formed in less than 5 seconds after delivery of the content of the two compartment device. The compositions were spread on a weighing dish so that a 1 mm layer of the biomaterials are formed. The weighing dish containing the reacting solutions was then placed at 37° C. in a humified atmosphere and cured for 10 min. 3 discs with a diameter of 1.2 cm are cut out of each film. The specimens were placed in tubes containing phosphate buffered solution (PBS) and placed in an incubator at 37° C. Biomaterials were removed from the tubes with help of a spatula at different time points. The biomaterials were carefully dried using tissue paper to remove any excess of water and then weighed. The biomaterials were then placed back into their respective tubes and placed back in the incubator. The swelling reached a value of 0.87±0.11 for the biomaterial formed from the composition of example 1a and 0.32±0.06% for the biomaterial formed from the composition of example 1b after 2 days in PBS at 37° C. Both Biomaterials had completely dissolved within 28 to 35 days (FIGS. 1 and 2).

Example 6

Compression Test 8 specimens of biomaterials formed from composition 1 as described in example 1a and 8 specimens of biomaterials formed from composition 2 as described in example 1b were prepared by filling 100 μl of compositions 1 and 2 into a cut 1 ml syringe. The biomaterials were cured for 5-10 min and then removed from their mold. Cylinders with a diameter of 5 mm and a height of 11.5 mm were obtained. Four biomaterials were placed in 10 mM PBS at pH 7.4 and four biomaterials were put in a dry tube. The tubes were incubated at 37° C. for 24 h. As the gelation time with a basic solution having a pH of 9.8 and 10.4, respectively, was too fast to form homogeneous specimens, the pH of the basic solution was lowered to pH 9.6. The samples were measured with a "Zwick Materialprüfung 1456" instrument. The Young's Modulus (elastic modulus) was determined with a 50 N load cell, the ultimate strength with a 20 kN load cell. The pre-load speed was increased from 0.05 to 0.1 mm/s and the waiting time was reduced to 3 s. The Young's modulus was measured at 3% compression but at a speed of 0.08 mm/s. The same speed was applied with the 20 kN load cell for pressure recording until the material cracked. Specimens of each biomaterials were compressed in dry state and after 24 h incubation in PBS. None of the biomaterials were destroyed in its dry state (stored in air at 37° C. for 24 h) when compressed up to 99%. In the wet state, the pressure at failure was 3.8±2.5 Nmm−2 for the biomaterial formed from composition 1 and 1.51±0.17 Nmm−2 for the biomaterial formed from composition 2. The % of compression at failure was 91±3% for the biomaterial formed from composition 1 and 88±2% for the biomaterial formed from composition 2. The Young's Modulus was 0.125±0.005 for the biomaterial formed from composition 1 and 0.10±0.00 Nmm−2 for the biomaterial formed from composition 2 in the wet state. In the dry state, the Young's modulus of the biomaterial formed from composition 2 was with a value of 0.561±0.152 Nmm−2 higher than of the biomaterial formed from composition 1 which exhibited a Young's modulus of 0.152±0.024 Nmm−2.

Example 7

Adhesive and Cohesive Strength of Biomaterials

The adhesive and cohesive strength of the biomaterials were examined in a burst test. Burst Test measurements were performed according to ASTM F-2329-04 (Standard test for burst strength of surgical sealants. A relative pressure sensor (DeltaOhm TP704-2BGI) has been used with a measuring range from 0-2 bar (maximal over-pressure 4 bar) and a resolution of 0.1 mbar. A syringe pump with a constant flow has been used as a fluid pump (Alaris, Asena Ohio). For burst pressure testing, the composition 8 and Duraseal® prepared as described in example 1h and 1i were applied to a humid collagen membrane. In order to guarantee equal sample shape, the collagen membrane was placed under a mask, through which the sealant is applied. The samples were then allowed to cure before they were removed carefully from the mask. After measuring sample thickness and weight, samples were clamped into the testing device and tested separately. The increasing pressure, which acted directly on the sealant through a prefabricated hole in the collagen, was measured constantly. After the sealant was burst, the pump could be turned off and evaluation of the collected data could be achieved. To allow for a comparison of the particular burst strengths of different samples, their thickness was measured before testing and normalized to 1 mm. Burst pressure testing of the two synthetic surgical sealants demonstrated clear differences in their resistance to failure. While biomaterial formed from composition 8 burst at an average pressure of 240 mmHg, DuraSeal® burst at an average pressure of 74 mmHg. The rate of cohesive failure for both sealants was 90%, which demonstrated a good adherence to the collagen membrane used in the test.

Example 8

Surgical Sealing of Sheep Dura

The dura mater of a sheep which had been sacrificed 3 hours was dissected. The skin was removed using a scalpel and a rectangular shape was cut into the skull using a bone blade. The skull was lifted and because the dura was still partly attached to the skull, the dura was carefully excised from the skull and placed back on the brain. Compositions 1 and 2 (as described in example 1a and 1b) were spread as a thin film on the dura and let to cure for 1 min. No leakage of fluids was observed. A round flat spatula was used to try and remove/peel the cured material off of the dura. The gel appearance, the gelation time, and adhesiveness were quantitatively assessed on a scale of 1-5. For gel appearance, grade 1 correspond to an inhomogeneous gel. Grade 2 corresponds to a gel that was mainly rough, grade 3 to a gel that had some rough parts, and grade 5 to a homogeneous smooth gel. For gelation time, grade 1 corresponds to about 50-100% of the composition running off. Grade 2 corresponds to about 25-50% of the composition running off, grade 3 to about 5-10% of the composition running off and grade 5 about 0-5% of the composition running off. For adhesiveness, grade 1 means that the gel peeled off with no force, grade 2 that the gel peeled off with low force, grade 3 that a medium force needed to be applied to remove the gel, grade 4 that very little of the gel pealed off, and grade 5 that none of the gel is removed. For composition 2 the pH was increased to 10.4 in order to decrease the gelation time. For comparison, the compositions were also applied to wet collagen membranes as well as directly to the brain. Both biomaterials formed from the compositions were found to adhere very well to the dura mater (biomaterial formed from composition 1-grade 4, biomaterial formed from composition 2-grade 3). The adhesiveness of the biomaterial to the dura mater was found to be much better than the adhesiveness to collagen membranes. In contrary, when applying the biomaterial to ovine brain (covered with pia mater and arachnoid layer) it could be peeled off easily. Composition 1 gelled quickly (grade 4) and therefore at the end of application some rough parts were created due to semi-gelled material being in contact with the spreader (grade 4 for gel appearance), composition 2, on the other hand, gelled rather slowly (grade 2), even when the pH of the basic solution was increased to 10.4 and not all the product was staying at the place of application but flowed off to the side, especially if the dura was not horizontal. Nevertheless, where the material was applied, a thin layer of material remained. Within 30 s, the material formed a tough and non-sticky hydrogel (grade 5 for gel appearance).

Example 9

Sheep Durotomy Model

The dura mater of an anaesthized sheep was exposed and a 2-cm incision was made in the dura and arachnoid so that cerebrospinal fluid leakage occurred. The defect was loosely repaired using 4/0 polypropylene suture but leaving a 1 mm gap. Composition 8 as described in example 1h was used with the following method.

Sterilization of Components

All applicator components, pouches, glass vials and closures were sterilized by gamma-irradiation at a dose of 21.8 kGy. Thereafter any handling of sterile material was performed in a sterile hood. Buffers and the tetronic-tetraacrylate solution were sterile filtered through 0.22 ▯m PES syringe filters. PEG-SH-5 was provided non-sterile in the kit and filtered through a 0.22 ▯m PES syringe filter after reconstitution with tetronic-tetraacrylate during the kit preparation.

Preparation of Buffers

The basic solution was prepared by dissolving 1.59 g sodium carbonate in 50 ml aqua ad injectable. The recorded pH was 11.38.

The Tetronic-acrylate solution was prepared by dissolving 471 mg tetronic-tetraacrylate in 3 ml of 5 mM HCl containing 0.05 mg/ml methylene blue. The reconstitution was achieved by vortexing 10-20 s, storing the solution at 4° C. for 10 min and centrifuging for 5 min at 2500 rpm. The 5 mM HCl solution was prepared from a 100 mM HCl solution by dilution with aqua ad injectabile. Methlyene blue was prepared as a 10 mg/ml methylene blue in 5 mM HCl solution and then diluted with 5 mM HCl.

Aseptic Filling and Packaging of Kit

The double syringe was assembled with pistons prior to sterilization. 400 µl of sodium carbonate were filled into the smaller compartment of the syringe and packed together with 4 spray heads and a plunger into pouch 1. The PEG-SH-5-component was prepared by weighing 192 mg of polymer into a glass vials. The glass vial was whipped with ethanol and the powder poured into a sterile glass vial without touching the outside. The vial was closed with a crimp cap. The tetronic-tetraacrylate solution was taken up into a 20 ml syringe and 3.3 ml were transferred into 5 ml syringe via a syringe-to-syringe coupler. The syringe was closed with a combi-stopper. The vial, the 5 ml syringe, a blue and a pink needle and a syringe filter were packed into pouch 2 and heat-sealed. Pouch 1 and 2 were pooled into a larger pouched and heat-sealed. The kits were stored at less than −15° C. to −25° C. and shipped on dry ice.

On the day of the experiment, the kit was removed from storage and placed at room temperature until completely thawed. At the time of use, the kit was opened in the sterile field. The tetronic-tetraacrylate solution was transferred into the vial containing the PEG-SH-5-powder. The powder was reconstituted by gently agitating the vial during 1-2 min. The mixture was taken up into the syringe again and the syringe was connected to a sterile filter and a blue needle and transferred into the larger compartment of the double syringe. The dispenser was attached to the double syringe and remaining air was expelled from the double syringe. The spray nozzle was placed onto the double syringe and the applicator was now ready to use.

The composition was sprayed over the dural defect and the biomaterial solidified in less than 5 seconds. The dural defect was carefully checked for reappearance of CSF leak. The sealant was able to intraoperatively stop the fluid leakage. The material was still present after 1 week and was completely resorbed after 12 weeks.

Example 10

Testing of Thermogelling Properties of Tetronic-Acrylate in High Concentrations

The gelation properties of composition 11 (as described from example 1k) and composition 12 (as described from example 1l) were compared, both in conjunction with linear PEG-SH 3.4 kDa. Gel formation was expected to occur through chemical cross-linking in composition 11 and through physical means (thermo-gelling) followed by chemical cross-linking in composition 12.

Composition 11 gelled in 1.5 minutes after a 30 second syringe-to-syringe mixing and had a set time of 2-3.5 minutes after applying the solution into a weighing dish through a needle. In case of composition 12, a gel was formed when the gel was applied to a weighing dish warmed by a surrounding water bath at 37° C. and run-down of the material was prevented. However, the set time was increased to 4-55 minutes and therefore longer than for composition 11. It was postulated that the high viscosity during the chemical curing hindered the molecules in their movement which therefore slowed down the chemical reaction.

Example 11

Influence of pH on Reaction Kinetics

Figure 3:
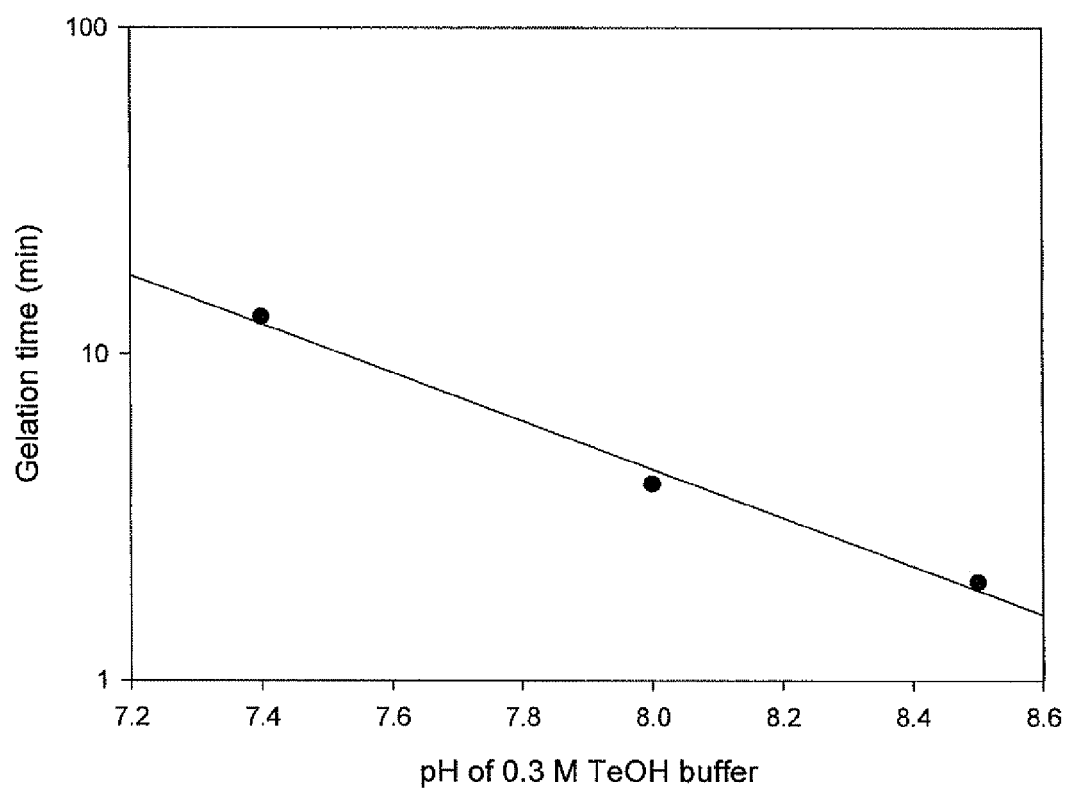
FIG. 3 is a graph of gellation time (minutes) versus pH, which shows the influence of buffer on gelation time for composition 10 prepared with TEA-buffer at pH 7.4, 8 and 8.5.
Figure 4:
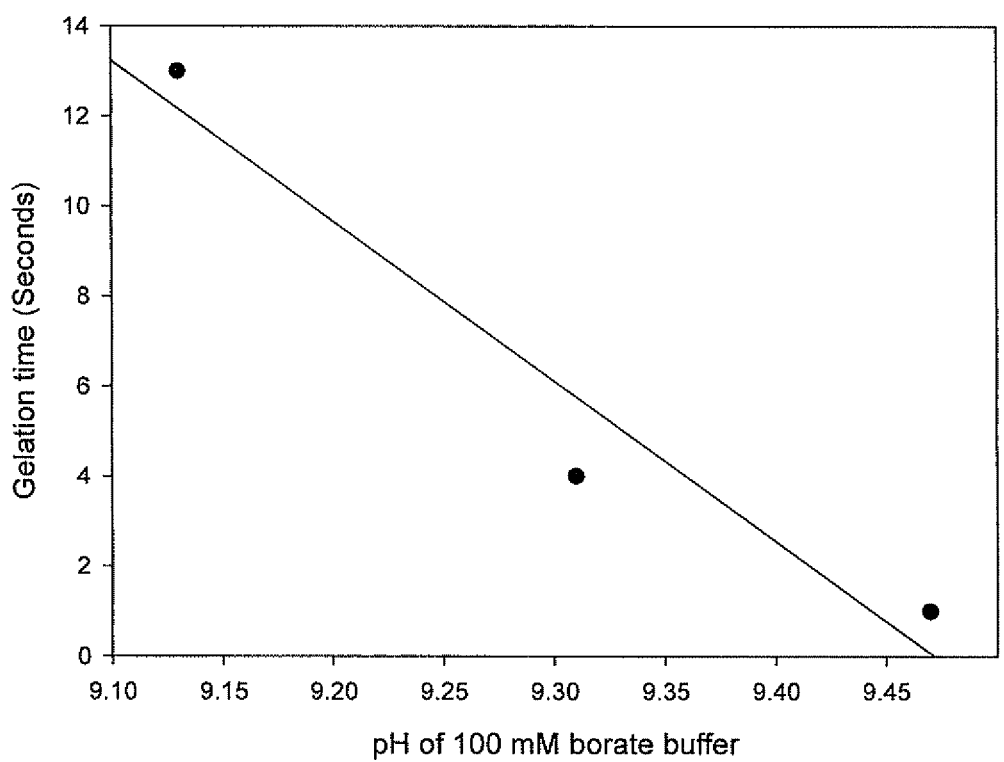
FIG. 4 is a graph of gellation time (seconds) versus pH, which shows the influence of buffer on gelation time for composition 13 prepared with a borate buffer at pH 9.13, 9.32 and 9.47.

The gelation time of a composition 10 (as prepared in example 1j) versus the pH of the buffer solution is depicted in FIG. 3. This shows that the gelation time decreases with increasing pH. The same increase behavior was observed for composition 13 (prepared as described in example 1m) (see FIG. 4).

We claim:

1. A composition comprising a first and a second precursor molecule, wherein:
   i) the first precursor molecule is poly(ethylene oxide) having x nucleophilic groups selected from the group consisting of thiol and amino groups, wherein x is greater than or equal to 2;
   ii) the second precursor molecule is of the general formula:

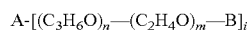

A-[(C$_3$H$_6$O)$_n$—(C$_2$H$_4$O)$_m$—B]$_i$ wherein m and n are integers from 1 to 200;
   i is greater than 2;
   A is a branch point; and
   B is a conjugated unsaturated group.

2. The composition of claim 1 wherein x is equal to 4.

3. The composition of claim 2 wherein the first precursor molecule is pentaerythritol poly(ethylene glycol)ether tetra-sulfhydryl.

4. The composition of claim 3 wherein pentaerythritol poly(ethylene glycol)ether tetra-sulfhydryl has a molecular weight in the range of about 2 to 20 kD.

5. The composition of claim 1 wherein B of the second precursor molecule is an acrylate group.

6. The composition of claim 1 wherein the branch point A of the second precursor molecule is selected from the group consisting of carbon, glycerol, pentaerythritol, dipentaerythritol and ethylene diamine.

7. The composition of claim 1 wherein the first precursor molecule is pentaerythritol poly(ethylene glycol)ether tetra-sulfhydryl and wherein B of the second precursor molecule is an acrylate group and wherein the branch point A of the second precursor molecule is ethylene diamine.

8. The composition of claim 1 wherein the second precursor molecule has a molecular weight in the range of about 10 to 25 kD.

9. The composition of claim 1 further comprising a base.

10. The composition of claim 9 wherein the base is sodium carbonate.

11. The composition of claim 1 further comprising a colorant selected from the group consisting of methylene blue, lissamin green and fast green.

12. A method for making a biomaterial comprising the steps of:
i) providing a first precursor molecule which is poly(ethylene oxide) having x nucleophilic groups selected from the group consisting of thiol and amino groups, wherein x is greater than or equal to 2;
ii) providing a second precursor molecule which is of the general formula:

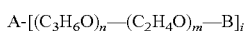

wherein m and n are integers from 1 to 200;
i is greater than 2;
A is a branch point;
B is a conjugated unsaturated group; and
iii) reacting the precursor molecules of steps i) and ii) in the presence of a basic solution to form the biomaterial, wherein the biomaterial is in the form of a crosslinked three dimensional network.

13. The method of claim 12 wherein the first precursor molecule and the second precursor molecule are dissolved in an aqueous buffered solution having an acidic pH before step iii).

14. The method of claim 13 wherein the biomaterial is formed in less than ten seconds.

15. The method of claim 12 wherein the reaction of step iii) occurs at a pH in the range of between 9 to 13.

16. A biomaterial formed from a composition comprising a first and a second precursor molecule, wherein:
i) the first precursor molecule is poly(ethylene oxide) having x nucleophilic groups selected from the group consisting of thiol and amino groups, wherein x is greater than or equal to 2;
ii) the second precursor molecule is of the general formula:

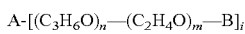

wherein m and n are integers from 1 to 200;
i is greater than 2;
A is a branch point; and
B is a conjugated unsaturated group.

17. The biomaterial of claim 16 wherein B of the second precursor molecule is an acrylate group and wherein the branch point A of the second precursor molecule is ethylene diamine.

18. The biomaterial of claim 16 wherein the first precursor molecule is pentaerythritol poly(ethylene glycol)ether tetra-sulfhydryl.

19. The biomaterial of claim 16 further comprising a colorant selected from the group consisting of methylene blue, lissamin green and fast green.

20. A method for reducing, inhibiting or containing loss of a biological fluid or gas in a patient in need thereof, comprising applying to a tissue in the patient a composition comprising a first and a second precursor molecule, wherein:
i) the first precursor molecule is poly(ethylene oxide) having x nucleophilic groups selected from the group consisting of thiol and amino groups, wherein x is greater than or equal to 2;
ii) the second precursor molecule is of the general formula:

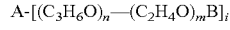

wherein m and n are integers from 1 to 200;
i is greater than 2;
A is a branch point; and
B is a conjugated unsaturated group;
wherein the first and second precursor molecule crosslink at physiological temperature over a period of time following application.

21. The method of claim 20 wherein the tissue is a biological membrane.

22. The method of claim 20 wherein B of the second precursor molecule is an acrylate group and wherein the branch point A of the second precursor molecule is ethylene diamine.

23. The method of claim 20 wherein the first precursor molecule is pentaerythritol poly(ethylene glycol)ether tetra-sulfhydryl.

24. The composition of claim 1 in a kit for forming a biomaterial, wherein the first precursor molecule is in a first container and the second precursor molecule is in a second container.

25. The kit of claim 24 further comprising a third container comprising a basic solution.

26. The kit of claim 25 further comprising a dual compartment syringe.

27. The kit of claim 24 wherein B of the second precursor molecule is an acrylate group and wherein the branch point A of the second precursor molecule is ethylene diamine.

28. The kit of claim 24 wherein the first precursor molecule is pentaerythritol poly(ethylene glycol)ether tetra-sulfhydryl.

29. The composition of claim 1, wherein the swelling of the biomaterial formed upon reaction of the first precursor molecule and the second precursor molecule in PBS buffer solution at 37° C. is less than 100% by weight after one day.

30. The composition of claim 1, wherein the swelling of the biomaterial formed upon reaction of the first precursor molecule and the second precursor molecule in PBS buffer solution at 37° C. is less than 125% by weight after seven days.

31. The method of claim 12, wherein the swelling of the biomaterial in PBS buffer solution at 37° C. is less than 100% by weight after one day.

32. The method of claim 31, wherein the swelling of the biomaterial in PBS buffer solution at 37° C. is less than 125% by weight after seven days.

33. The biomaterial of claim 16, wherein the swelling of the biomaterial in PBS buffer solution at 37° C. is less than 100% by weight after one day.

34. The biomaterial of claim 33, wherein the swelling of the biomaterial in PBS buffer solution at 37° C. is less than 125% by weight after seven days.

35. The method of claim 20, wherein the swelling of the biomaterial formed by the crosslinking of the first precursor molecule and the second precursor molecule in PBS buffer solution at 37° C. is less than 100% by weight after one day.

36. The method of claim 35, wherein the swelling of the biomaterial formed by the crosslinking of the first precursor molecule and the second precursor molecule in PBS buffer solution at 37° C. is less than 125% by weight after seven days.

37. The composition of claim 4, wherein pentaerythritol poly(ethylene glycol)ether tetra-sulfhydryl has a molecular weight in the range of about 5 to 10 kD.

38. The composition of claim 8, wherein the second precursor molecule has a molecular weight in the range of about 14 to 18 kD.

39. The method of claim 12, wherein the first precursor molecule has a molecular weight in the range of about 2 to 20 kD.

40. The method of claim 39, wherein the first precursor molecule has a molecular weight in the range of about 5 to 10 kD.

41. The method of claim 12, wherein the second precursor molecule has a molecular weight in the range of about 10 to 25 kD.

42. The method of claim 41, wherein the second precursor molecule has a molecular weight in the range of about 14 to 18 kD.

43. The biomaterial of claim 16, wherein the first precursor molecule has a molecular weight in the range of about 2 to 20 kD.

44. The biomaterial of claim 43, wherein the first precursor molecule has a molecular weight in the range of about 5 to 10 kD.

45. The biomaterial of claim 16, wherein the second precursor molecule has a molecular weight in the range of about 10 to 25 kD.

46. The biomaterial of claim 45, wherein the second precursor molecule has a molecular weight in the range of about 14 to 18 kD.

47. The method of claim 20, wherein the first precursor molecule has a molecular weight in the range of about 2 to 20 kD.

48. The method of claim 47, wherein the first precursor molecule has a molecular weight in the range of about 5 to 10 kD.

49. The method of claim 20, wherein the second precursor molecule has a molecular weight in the range of about 10 to 25 kD.

50. The method of claim 49, wherein the second precursor molecule has a molecular weight in the range of about 14 to 18 kD.

51. The composition of claim 1, wherein the concentration of the second precursor molecule is in a range between 8% and 18% w/w of the composition.

52. The composition of claim 51, wherein the concentration of the second precursor molecule is in a range between 10% and 16% w/w of the composition.

53. The composition of claim 52, wherein the concentration of the second precursor molecule is in a range between 12% and 14% w/w of the composition.

54. The method of claim 12, wherein the concentration of the second precursor molecule is in a range between 8% and 18% w/w of the biomaterial.

55. The method of claim 54, wherein the concentration of the second precursor molecule is in a range between 10% and 16% w/w of the biomaterial.

56. The method of claim 55, wherein the concentration of the second precursor molecule is in a range between 12% and 14% w/w of the biomaterial.

57. The biomaterial of claim 16, wherein the concentration of the second precursor molecule is in a range between 8% and 18% w/w of the biomaterial.

58. The biomaterial of claim 57, wherein the concentration of the second precursor molecule is in a range between 10% and 16% w/w of the biomaterial.

59. The biomaterial of claim 58, wherein the concentration of the second precursor molecule is in a range between 12% and 14% w/w of the biomaterial.

60. The method of claim 20, wherein the concentration of the second precursor molecule is in a range between 8% and 18% w/w of the composition.

61. The method of claim 60, wherein the concentration of the second precursor molecule is in a range between 10% and 16% w/w of the composition.

62. The method of claim 61, wherein the concentration of the second precursor molecule is in a range between 12% and 14% w/w of the composition.

63. The composition of claim 1, wherein the biomaterial formed upon reaction of the first precursor molecule and the second precursor molecule exhibits an average burst pressure of at least 240 mmHg as measured according to ASTM F-2329-04, the standard test for the burst strength of surgical sealants.

64. The method of claim 12, wherein the biomaterial exhibits an average burst pressure of at least 240 mmHg as measured according to ASTM F-2329-04, the standard test for the burst strength of surgical sealants.

65. The biomaterial of claim 16, wherein the biomaterial exhibits an average burst pressure of at least 240 mmHg as measured according to ASTM F-2329-04, the standard test for the burst strength of surgical sealants.

66. The method of claim 20, wherein the biomaterial formed upon crosslinking of the first precursor molecule and the second precursor molecule exhibits an average burst pressure of at least 240 mmHg as measured according to ASTM F-2329-04, the standard test for the burst strength of surgical sealants.

* * * * *

UNITED STATES PATENT AND TRADEMARK OFFICE
CERTIFICATE OF CORRECTION

PATENT NO. : 8,961,947 B2  
APPLICATION NO. : 12/102157  
DATED : February 24, 2015  
INVENTOR(S) : Annemie Rehor and Simona Cerritelli Page 1 of 1

It is certified that error appears in the above-identified patent and that said Letters Patent is hereby corrected as shown below:

Claim 20, column 32, line 12; replace "A-[(C3H6O)n-(C2H4O)mB]i" with --A-[(C3H6O)n-(C2H4O)m-B]i--.

Signed and Sealed this  
Eighth Day of March, 2016

Michelle K. Lee  
*Director of the United States Patent and Trademark Office*